(12) United States Patent
Ikeuchi et al.

(10) Patent No.: US 9,187,579 B2
(45) Date of Patent: Nov. 17, 2015

(54) PARTICLE-SHAPED WATER ABSORBING AGENT AND METHOD FOR PRODUCING THE SAME

(75) Inventors: Hiroyuki Ikeuchi, Hyogo (JP);
Hirotama Fujimaru, Hyogo (JP);
Makoto Nagasawa, Nara (JP);
Kazuhiko Sakamoto, Hyogo (JP);
Shigeru Sakamoto, Hyogo (JP);
Kazushi Torii, Hyogo (JP); Ryoko Tahara, Ibaraki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 288 days.

(21) Appl. No.: 12/524,989

(22) PCT Filed: Feb. 4, 2008

(86) PCT No.: PCT/JP2008/051777
§ 371 (c)(1),
(2), (4) Date: Jul. 29, 2009

(87) PCT Pub. No.: WO2008/096713
PCT Pub. Date: Aug. 14, 2008

(65) Prior Publication Data
US 2010/0009846 A1    Jan. 14, 2010

(30) Foreign Application Priority Data

Feb. 5, 2007 (JP) ................. 2007-025091
Mar. 27, 2007 (JP) ................. 2007-080695
Jul. 6, 2007 (JP) ................. 2007-178031

(51) Int. Cl.
*B01J 20/22* (2006.01)
*B01J 20/26* (2006.01)
(Continued)

(52) U.S. Cl.
CPC ............... *C08F 2/44* (2013.01); *C08F 220/06* (2013.01); *C08L 33/02* (2013.01);
(Continued)

(58) Field of Classification Search
USPC .............. 502/400, 401, 402; 526/91, 93, 94, 526/317.1; 428/402
See application file for complete search history.

(56) References Cited

U.S. PATENT DOCUMENTS 5,298,570 A    3/1994  Tahara et al.
6,103,820 A *  8/2000  Blankenburg et al. ........ 524/767
(Continued)

FOREIGN PATENT DOCUMENTS

CN    1163900    11/1997
CN    1610707    4/2005
(Continued)

OTHER PUBLICATIONS

Hunter Associates Laboratory, Inc., "Insight on Color: Hunter L, a, b Color Scale." vol. 8, No. 9 (Jun. 2008), (c)2008.*
(Continued)

*Primary Examiner* — Stanley Silverman
*Assistant Examiner* — Daniel Berns
(74) *Attorney, Agent, or Firm* — Amin, Turocy & Watson, LLP

(57) ABSTRACT

An object of the present invention is to provide a particle-shaped water absorbing agent having a remarkably improved surface color and excellent water-absorbing properties (better water absorption capacity, and lower water soluble content and residual monomer content) at the same time. In order to attain the object, a particle-shaped water absorbing agent according to the present invention is a particle-shaped water absorbing agent whose main component is a polyacrylic acid and/or a salt thereof, the particle-shaped water absorbing agent having a surface color of Hunter b value in a range of −5 to 10, and having a cross-linking absorption property index (CPI) in a range of 1 to 100, the CPI defined by the following two equations:

$GEX=(GVs+17)/Ln$ (water soluble content);    Equation 1:

$CPI=(GEX/\text{residual monomer content})\times 100$    Equation 3:

where GVs is gel volume in saline, Ln (water soluble content) is a logarithm natural of water soluble content.

9 Claims, 1 Drawing Sheet

(51) Int. Cl.
  *C08F 20/06*   (2006.01)
  *C08F 2/44*    (2006.01)
  *C08F 220/06*  (2006.01)
  *C08L 33/02*   (2006.01)
  *A61F 13/53*   (2006.01)
  *C08F 222/10*  (2006.01)
  *C08K 5/00*    (2006.01)
  *C08L 71/02*   (2006.01)

(52) U.S. Cl.
  CPC .............. *A61F 2013/530583* (2013.01); *C08F 222/1006* (2013.01); *C08K 5/0008* (2013.01); *C08L 71/02* (2013.01); *Y10T 428/2982* (2015.01)

(56) References Cited

U.S. PATENT DOCUMENTS

| | | | |
|---|---|---|---|
| 6,444,744 | B1 | 9/2002 | Fujimaru et al. |
| 6,576,713 | B2 * | 6/2003 | Ishizaki et al. .............. 525/329.7 |
| 6,906,159 | B2 | 6/2005 | Dairoku et al. |
| 2002/0040095 | A1 | 4/2002 | Dairoku et al. |
| 2004/0092688 | A1 * | 5/2004 | Dairoku et al. ............ 526/317.1 |
| 2004/0110914 | A1 | 6/2004 | Nakahara et al. |
| 2004/0181031 | A1 | 9/2004 | Nogi et al. |
| 2005/0013865 | A1 | 1/2005 | Nestler et al. |
| 2005/0085604 | A1 | 4/2005 | Handa et al. |
| 2006/0167198 | A1 | 7/2006 | Sasabe et al. |
| 2007/0066167 | A1 | 3/2007 | Wada et al. |
| 2007/0123658 | A1 | 5/2007 | Torii et al. |
| 2007/0141338 | A1 | 6/2007 | Ishizaki et al. |
| 2007/0232760 | A1 * | 10/2007 | Fujimaru et al. ........... 525/329.7 |
| 2008/0075937 | A1 | 3/2008 | Wada et al. |
| 2010/0113264 | A1 * | 5/2010 | Tsurumi et al. ............... 502/402 |
| 2010/0308263 | A1 | 12/2010 | Torii et al. |

FOREIGN PATENT DOCUMENTS

| | | |
|---|---|---|
| CN | 1810297 | 8/2006 |
| CN | 1856331 | 11/2006 |
| EP | 1 178 059 | 2/2002 |
| EP | 1462473 A1 | 9/2004 |
| EP | 1 683 813 | 7/2006 |
| JP | 01-275661 | 11/1989 |
| JP | 04-331205 | 11/1992 |
| JP | 05-086251 | 4/1993 |
| JP | 2000-230129 | 8/2000 |
| JP | 2000-313796 | 11/2000 |
| JP | 2000-327926 | 11/2000 |
| JP | 2001-011328 | 1/2001 |
| JP | 2002-212204 | 7/2002 |
| JP | 2003-052742 | 2/2003 |
| JP | 2003-206381 | 7/2003 |
| JP | 2003-246810 | 9/2003 |
| JP | 2005-186016 | 7/2005 |
| JP | 2006-116535 | 5/2006 |
| WO | 00/55245 A1 | 9/2000 |
| WO | 03/051940 A1 | 6/2003 |
| WO | 2005/054356 A1 | 6/2005 |
| WO | 2006033477 | 3/2006 |
| WO | 2006-109842 A1 | 10/2006 |

OTHER PUBLICATIONS

European Search Report for 08710756.1 Mailed Mar. 10, 2011.
Japanese Search Report mailed on May 1, 2008 corresponding to PCT Application No. PCT/JP2008/051777 filed on Feb. 4, 2008.
Written Opinion of the International Searching Authority mailed on May 1, 2008 corresponding to PCT Application No. PCT/JP2008/051777 filed on Feb. 4, 2008.
Chinese Office Action for Application No. 200880003930.5 issued on Sep. 15, 2011.
Japanese Office Action for Japanese Application No. 2008-557104 mailed on Jul. 17, 2012.
European Third Party Observation for European Application No. 08710756.1 dated Jul. 18, 2012.
Office Action of Third Party Observations Against EP 08710756.1 Dated Mar. 4, 2014, 19 pgs.
Notification of First Office Action for Chinese Patent Application No. 201210147216.1 Dated Nov. 29, 2013, 14 pgs.
Office Action of Notification of Reasons for Refusal for Japanese Patent Application No. 2008-557104 Dated May 7, 2014, 9 pgs.

* cited by examiner

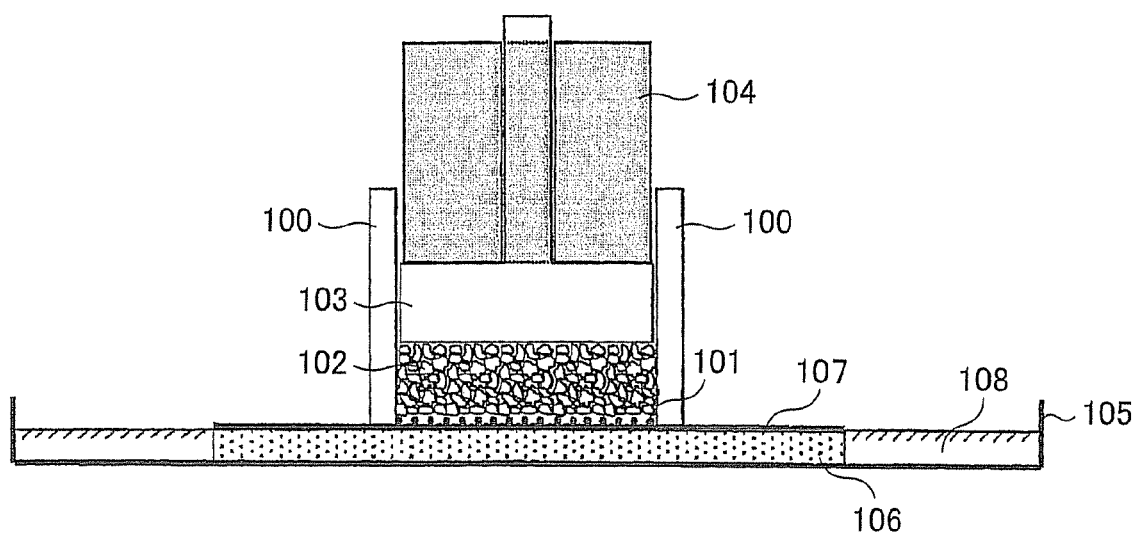

PARTICLE-SHAPED WATER ABSORBING AGENT AND METHOD FOR PRODUCING THE SAME

TECHNICAL FIELD

The present invention relates to a particle-shaped water absorbing agent whose main component is an absorbing resin of a polyacrylic acid and/or a salt thereof and producing method of the same. More particularly, the present invention relates to a particle-shaped water absorbing agent which is a virtually white particle-shaped water absorbing agent, has excellent tolerance against urine (gel deterioration prevention property), gives sensation of cleanness due to the white surfaces of particles, and has a high property and excellent stability, and to a producing method of the same.

BACKGROUND ART

Recently, a water absorbing agent having a high water absorbency has been developed and variously used for mainly disposable usage as absorbing goods such as paper diapers, sanitary napkins, and the like, moreover, as water retaining agents for agriculture/horticulture uses, as water-stop materials for industrial uses, and the like. Many monomers and hydrophilic polymers have been proposed as a material of such water absorbing agent. Especially, an absorbing resin of a polyacrylic acid and/or a salt thereof, for which a polyacrylic acid and/or a salt thereof as a monomer is used, has been most used for industrial purposes due to its high water-absorbing property.

Conventionally, as a water-absorbing property which is desirable for the water absorbing agent, there has been known various properties (parameters) such as absorbency against no pressure, absorbency against pressure, absorption speed, liquid permeability against no pressure, liquid permeability against pressure, impact resistance, tolerance against urine, fluidity, gel strength, grain size, and the like. Moreover, even in the same property (for example, absorbency under no load), a variety of definitions (parameter measurement technique) has been proposed from various viewpoints.

These water absorbencies are mainly used for sanitary/hygienic materials such as paper diapers, sanitary napkins, and the like. Therefore, it is required that the water absorbing agent be white before carried from a factory, in order to give sensation of cleanness and in order not to give uncomfortable sensations because of coloring when the powdery water absorbing agent is compounded with white pulps in the sanitary/hygienic material. In addition, the water absorbing agent is generally white powder. It has been known that even after shipped from a factory, the water absorbing agent is colored (from yellow to brown) as time passes by while being stored or transported, or moreover, when used for the sanitary/hygienic materials. Therefore, it is required that the water absorbing agent be white in the case where absorbing goods are stored over a prolonged time. In recent years, content ratio (percentage by weight) of the absorbing resin in the sanitary/hygienic material tends to increase. Accordingly, the color problem becomes more important.

In order to improve such problem, the following methods are suggested: a method in which an alkyl phosphate or a salt thereof is subsequently added to the absorbing resin (Patent Citation 1, 2); a method in which a total amount of a hydroquinone and benzoquinone in an acrylic acid is prepared not to be more than 0.2 ppm by weight (Patent Citation 3); a method in which a methoxyphenol compound in an acrylic acid is prepared in a range of 10 to 160 ppm by weight (Patent Citation 4); a method in which an inorganic reducing agent is added to the absorbing resin (Patent Citation 5); a method in which an organic carboxylic acid or a salt thereof is added to the absorbing resin (Patent Citation 6, 7, 8); a method in which a tocopherol (Patent Citation 9) or a sterically-hindered phenol (Patent Citation 10) is used as a polymerization inhibitor in an acrylic acid for polymerization; a method in which a metal chelating agent is added in producing an absorbing resin (Patent Citation 11, 12); and a method in which an acrylic acid monomer and/or a salt thereof is polymerized by a hydroxyperoxide and a reducing agent, and then processed by a silane coupling agent (Patent Citation 13). However, in any of the above methods, the color problem after the absorbing resin is produced is not sufficiently improved, and moreover, there still have been problems such as polymerization reactor control in producing the absorbing resin, property deterioration, and the like.

Conventionally, a methoxyphenol used in treating of unsaturated-monomers such as an acrylic acid and the like is generally used in a range of about 100 to 200 ppm by weight from the viewpoint of stability of storage and preservation. However, it is difficult to improve coloring status because of increase in the surface color of the absorbing resin due to the methoxyphenol. Meanwhile, in order to improve the surface color of the absorbing resin, a technique to control the methoxyphenol in a certain amount range has been proposed. However, when the absorbing resin is produced from the unsaturated-monomer through polymerization step, drying step, and the like steps at actual production facilities, the technique is insufficient to produce desired properties.

Especially, in order to remarkably improve the surface color of the absorbing resin, when the methoxyphenol is used, for example, by 20 ppm by weight at an actual production facility, it is extremely difficult to produce an absorbing resin having stability and high properties.

Moreover, in conventionally proposed methods using an additive agent or the like, when the whiteness of the surface color of particles becomes better, the polymerization control becomes difficult, and it causes problems such as increase in residual monomers and soluble contents, or the like.

More specifically, in the conventional methods, when absorbency is improved and an amount of the residual monomers is decreased, an amount of the soluble contents increases and the surface color of the particle-shaped water absorbing agent is colored. When the absorbency is improved and the amount of the soluble contents is decreased, the surface color is improved to some extent, but the improvement is not sufficient, and furthermore, the amount of the residual monomers increases.

As described above, it is difficult to satisfy either of the water-absorbing property (the absorbency, the amount of the soluble contents, and the amount of the residual monomers) and the surface color of the particle-shaped water absorbing agent (especially, yellow which is represented of b value) by the conventional methods such as radical control, addition of an oxidizing agent or reducing agent, control of an amount of impurity, or the like. In addition, a conventional method of adding a chelating agent, for example, has an advantage of preventing coloring for storage over time or under high temperature and humidity. However, because the additive agent has its own color, it is not sufficient to satisfy either of the drastic improvement of the surface color of the particle-shaped water absorbing agent and the water-absorbing property.

When the ratio of the absorbing resin and the particle-shaped water absorbing agent in an absorber is as low as 10 to 30% by weight, those problems are not obvious. However, in recent years, as a density of the absorbing resin becomes high (the ratio thereof in the absorber or the paper diapers is 40 to 100% by weight), those problems has come to the surface.

[Patent Citation 1] Japanese Unexamined Patent Publication, Tokukaihei, No. 5-86251 (published on Apr. 6, 1993)
[Patent Citation 2] Japanese Unexamined Patent Publication, Tokukaihei, No. 1-275661 (published on Nov. 6, 1989)
[Patent Citation 3] U.S. Pat. No. 6,444,744 (registered on Sep. 3, 2002)
[Patent Citation 4] International Publication No. 2003/51940 (published on Jun. 26, 2003)
[Patent Citation 5] International Publication No. 2000/55245 (published on Sep. 21, 2000)
[Patent Citation 6] Japanese Unexamined Patent Publication, Tokukai, No. 2000-327926 (published on Nov. 28, 2000)
[Patent Citation 7] Japanese Unexamined Patent Publication, Tokukai, No. 2003-52742 (published on Feb. 25, 2003)
[Patent Citation 8] Japanese Unexamined Patent Publication, Tokukai, No. 2005-186016 (published on Jul. 14, 2005)
[Patent Citation 9] International Publication No. 2003/53482 (published on Jul. 3, 2003)
[Patent Citation 10] International Publication No. 2005/54356 (published on Jun. 16, 2005)
[Patent Citation 11] Japanese Unexamined Patent Publication, Tokukai, No. 2003-206305 (published on Jul. 22, 2003)
[Patent Citation 12] Japanese Unexamined Patent Publication, Tokukai, No. 2003-206381 (published on Jul. 22, 2003)
[Patent Citation 13] Japanese Unexamined Patent Publication, Tokukaihei, No. 4-331205 (published on Nov. 19, 1992)

DISCLOSURE OF INVENTION

The present invention was accomplished in view of the aforementioned problem. An object of the present invention is to provide a particle-shaped water absorbing agent having a remarkably improved surface color and an excellent water-absorbing property, and a method for producing the water absorbing agent. That is, the object of the present invention is to satisfy both properties of the excellent water-absorbing property (improvement of absorbency, and reduction of a water soluble content and residual monomer) and improved whiteness (especially improved whiteness at the stage of production, at the stage just after shipping, and at the stage of delivery to a user) of the surface color of particles. The both properties in the particle-shaped water absorbing agent containing an absorbing resin as its main component are conventionally incompatible.

Moreover, another object of the present invention is to provide absorbing goods (e.g., diaper and an absorber) which can give high sensation of cleanness without causing leakage, slimy sensation, and wet sensation, the absorbing goods having such high particle-shaped water absorbing agent content that the particle-shaped water absorbing agent is contained therein for example by 40 to 100% by weight, or 50 to 100% by weight.

In order to attain the object, a particle-shaped water absorbing agent of the present invention is a particle-shaped water absorbing agent whose main component is a polyacrylic acid and/or a salt thereof, the particle-shaped water absorbing agent having a surface color of Hunter b value in a range of −5 to 10, and having a cross-linking absorption property index (CPI) in a range of 1 to 100, the CPI defined by the following two equations:

$$GEX=(GVs+17)/\mathrm{Ln} \text{ (water soluble content)}; \quad \text{Equation 1:}$$

$$CPI=(GEX/\text{residual monomer content})\times 100 \quad \text{Equation 3:}$$

where GVs is gel volume in saline, Ln (water soluble content) is a logarithm natural of water soluble content.

More specifically, the present invention provides the following particle-shaped water absorbing agents (i) and (iv):

(i) A particle-shaped water absorbing agent comprising: a polyacrylic acid and/or a salt thereof as its main component; N-oxyl compound by 0.01 to 10 ppm by weight; and a methoxyphenol compound by 0 to 20 ppm by weight, preferably 10 ppm or below by weight, which is more preferably not included therein substantially (0 ppm by weight).

(ii) A particle-shaped water absorbing agent comprising: a polyacrylic acid and/or a salt thereof as its main component; a methoxyphenol compound by 0.01 to 20 ppm by weight; and a manganese compound by 0.01 to 10 ppm by weight (as $MnO_2$).

(iii) A particle-shaped water absorbing agent comprising: a polyacrylic acid and/or a salt thereof as its main component; a polyalkyleneglycol; and iron by iron content in a range of 0.001 to 5 ppm by weight, and (iv) A particle-shaped water absorbing agent comprising: a polyacrylic acid and/or a salt thereof as its main component; and a water-soluble thiodialkyl compound.

In order to attain the object, a method according to the present invention is a method for producing particle-shaped water absorbing agent, the method including the step of polymerizing an unsaturated-monomer aqueous solution containing an acrylic acid and/or a salt thereof as a main component thereof, the method satisfying any one of the followings:

1) the unsaturated-monomer aqueous solution contains N-oxyl compound by 0.01 to 10 ppm by weight based on an unsaturated monomer content thereof;

2) the unsaturated-monomer aqueous solution contains a methoxyphenol compound by 0.01 to 20 ppm by weight and a manganese compound by 0.01 to 10 ppm by weight (as $MnO_2$);

3) a polyalkyleneglycol of weight average molecular weight of 300 to 50000 and iron are prepared or added by a range of 0.01 to 10% by weight and in a range of 0.001 to 10 ppm by weight respectively in the unsaturated-monomer aqueous solution which contains the acrylic acid and/or the salt thereof as its main component, which is/are not polymerized or is/are polymerized incompletely; and 4) a water-soluble thiodialkyl compound is added in the unsaturated-monomer aqueous solution.

With these arrangements, it is possible to satisfy both properties of the excellent water-absorbing property (improvement of absorbency, and reduction of the water soluble content and residual monomer) and improved whiteness of the surface color of particles. The both properties in the particle-shaped water absorbing agent containing an absorbing resin as its main component are conventionally incompatible. In addition, it is possible to realize absorbing goods (e.g., diaper and an absorber) which can give high sensation of cleanness without causing leakage, slimy sensation, and wet sensation.

For a fuller understanding of the nature and advantages of the invention, reference should be made to the ensuing detailed description taken in conjunction with the accompanying drawings.

BRIEF DESCRIPTION OF DRAWINGS

FIG. 1 is a cross sectional view schematically illustrating a measuring apparatus for measuring absorption against pressure (AAP).

BEST MODE FOR CARRYING OUT THE INVENTION

A particle-shaped water absorbing agent contains a polyacrylic acid and/or a salt thereof as its main component, has a surface color of Hunter b value in a range of −5 to 10, more preferably −5 to 5, and further more preferably −3 to 3, and has a cross-linking absorption property index (CPI) in a range of 1 to 100, which is defined afterward.

Also, it is preferable that the particle-shaped water absorbing agent of the present invention have a surface color of Hunter L value in a range of 90 to 100.

Moreover, it is preferable that the particle-shaped water absorbing agent satisfy at least one of the followings:

(a) containing particles smaller than 150 µm in particle size by 0 to 5% by weight, and having a mass medium particle size (D50) in a range of 200 to 600 µm and a logarithmic standard deviation (sz) of particle size distribution in a range of 0.20 to 0.40;

(b) having an absorbency against pressure (AAP) of 20 g/g or more for 0.90 wt % saline under pressure 1.9 kPa or 4.8 kPa for 60 min; and (c) having a saline flow conductivity (SFC) of 5 (cm$^3$s $10^{-7}$/g) or more for 0.69 wt % saline.

Preferable means for achieving the particle-shaped water absorbing agent of the present invention is preferably exemplified as follows.

(A) First Embodiment

A method for producing a particle-shaped water absorbing agent and the particle-shaped water absorbing agent produced by the method, the method including the steps of polymerizing an unsaturated-monomer aqueous solution containing an acrylic acid and/or a salt thereof as its main component, so as to obtaining a hydrous gel polymer, and drying the hydrous gel polymer, wherein the unsaturated-monomer aqueous solution contains N-oxyl compound by 0.01 to 10 ppm by weight based on an unsaturated-monomer content thereof.

(B) Second Embodiment

A method for producing a particle-shaped water absorbing agent and the particle-shaped water absorbing agent produced by the method, the method including the steps of polymerizing an unsaturated-monomer aqueous solution containing an acrylic acid and/or a salt thereof as its main component, so as to obtaining a hydrous gel polymer, and drying the hydrous gel polymer, wherein the unsaturated-monomer aqueous solution contains a methoxyphenol compound by 0.01 to 20 ppm by weight and a manganese compound by 0.01 to 10 ppm by weight (as MnO$_2$) based on an unsaturated-monomer content thereof.

(C) Third Embodiment

A method for producing a particle-shaped water absorbing agent and the particle-shape water absorbing agent produced by the method, the method including adding or preparing a polyalkyleneglycol of weight average molecular weight of 300 to 50000 and iron by a range of 0.01 to 10% by weight and in a range of 0.001 to 10 ppm by weight respectively in an unsaturated-monomer aqueous solution which contains an acrylic acid and/or a salt thereof as its main component and which is not polymerized or is polymerized incompletely.

(D) Fourth Embodiment

A method for producing a particle-shaped water absorbing agent and the particle-shaped water absorbing agent produced by the method, the method including adding a water-soluble thiodialkyl compound in an absorbing resin of a polyacrylic acid and/or a salt thereof.

The present invention is more particularly described as follows.

(1) Particle-Shaped Water Absorbing Agent

A particle-shaped water absorbing agent of the present invention contains a polyacrylic acid and/or a salt thereof as its main component, having a surface color of a Hunter b value in a range of −5 to 5, more preferably −3 to 3, and having a CPI in a range of 1 to 100. More particularly, the particle-shape water absorbing agent having novel parameters of the present invention includes, as an example of means for achieving the present invention or as means for solving the above problems, the compounds or agents preferably exemplified in above first to fourth embodiments, and preferably further includes a polyvalent metal salt, an inorganic powder, or the like, which is preferably combined with the absorbing resin.

In the first embodiment of the present invention, a particle-shaped water absorbing agent contains at least N-oxyl compound in a range of 0.01 to 10 ppm by weight.

In the second embodiment of the present invention, a particle-shaped water absorbing agent contains at least a manganese compound in a range of 0.01 to 10 ppm by weight (preferably as MnO$_2$).

In the third embodiment of the present invention, a particle-shaped water absorbing agent contains at least polyalkyleneglycol in a range of 0.01 to 10% by weight and iron by iron content in a range of 0.001 to 5 ppm by weight.

In the fourth embodiment of the present invention, a particle-shaped water absorbing agent contains at least a water-soluble thiodialkyl compound in a range of 0.001 to 10% by weight.

In the present invention, a particle-shaped water absorbing agent means an absorbing fixation agent (also known as a gelatinizing agent) for aqueous liquid, the absorbing fixation agent preferably containing at least an absorbing resin of a polyacrylic acid and/or a salt thereof as its main component. Aqueous liquid is not only water but also may be urine, blood, fecal matter, waste fluid, wet and mist, ice, mixture of water and organic solvent or inorganic solvent, rain water, groundwater, and the like. The aqueous liquid is not especially limited as long as water is included. However, the particle-shaped water absorbing agent of the present invention is preferably an absorbing fixation agent for urine, particularly human urine.

The particle-shaped water absorbing agent of the present invention contains at least an absorbing resin of a polyacrylic acid/or a salt thereof as its main component preferably in a range of 70 to 99.9% by weight to the particle-shaped water absorbing agent, more preferably 80 to 99.7% by weight, and further more preferably 90 to 99.5% by weight. From a viewpoint of absorption speed and impact resistance of powder (particles), the particle-shaped water absorbing agent of the present invention preferably contains water as a component other than the water absorbing resin, and contains additives described later if necessary.

The absorbing resin of the polyacrylic acid and/or the salt thereof is a water-swelling/water-insoluble cross-linking agent polymer, which preferably includes the acrylic acid and/or the salt thereof in a range of 30 to 100 mol %, preferably 50 to 100 mol %, more preferably 70 to 100 mol %, and further more preferably 90 to 100 mol % in repeating unit (excluding a cross-linking agent). The water-swelling means that the after-mentioned absorbency is not less than 5 g/g, furthermore not less than 10 g/g. The water-insolubility means that the after-mentioned water-insoluble element is not more than 50%, moreover not more than 30%, and especially not more than 20%.

An acrylate or acrylic acid group as a repeating unit is a monovalent salt, preferably an alkali metal salt or ammonium salt, more preferably an alkali metal salt, and further more preferably a sodium salt. The acrylate or acrylic acid group is neutralized in a range of 0 to 100 mol %, preferably 20 to 100 mol %, more preferably 50 to 99 mol %, and further more preferably 60 to 90 mol %.

In the present invention, absorbing resins other than the absorbing resin of the polyacrylic acid and/or the salt thereof can be also used singularly or in combination. However, as an absorbing resin, the absorbing resin of the polyacrylic acid and/or the salt thereof is preferably used as a main component in a range of 50 to 100% by weight, more preferably 70 to 100% by weight, and further more preferably 90 to 100% by weight. Alternative absorbing resins, for example, are polyamine absorbing resins such as a polyethyleneimine based cross-linking material, a polyallylamine based cross-linking material, or the like, non-ion absorbing resins such as a polyacrylamide based cross-linking material, a polyethylene oxide based cross-linking material. In the present invention, the absorbing resin of the polyacrylic acid and/or the salt thereof is used as such compound.

In the particle-shaped water absorbing agent of the present invention, a chelating agent, a reducing agent, an oxidant inhibitor, or the like may be added in a range of 0.0001 to 2% by weight, preferably 0.001 to 1% by weight with respect to the particle-shaped water absorbing agent.

It is preferable that raw materials of the particle-shaped water absorbing agent (unsaturated-monomer, cross-linking agent, or the like) be a water-soluble compound. In the present invention, the water solubility means a compound having solubility to 100 ml of ion-exchanged water at normal pressure of 25±2° C., and being at least not less than 1 g, preferably not less than 5 g, and more preferably not less than 10 g.

(2) Monomer (Unsaturated Monomer)

The monomer (unsaturated monomer) in the present invention is an acrylic acid, a salt thereof or a mixture of the acrylic acid and salt thereof (especially monovalent salt), preferably in view of the properties of the resultant particle-shaped water absorbing agent. In case where the monomer includes the acrylic acid and salt thereof, it is preferable that the monomer contains, as a repeating unit of the water absorbing resin, the acrylic acid by 1 to 50 mol % to a total number of moles of the monomer, and it is also preferable that the monomer contains, as a repeating unit of the water absorbing resin, the salt thereof by 50 to 99 mol % to the total number of moles of the monomer. Note that neutralization of the salt thereof may be carried out by neutralization polymerization (polymerization of the acrylic acid monomer which is neutralized before the polymerization is carried out), or may be carried out after the polymerization of the acrylic acid (polyacrylic acid is neutralized during the polymerization or after the polymerization), or may be carried out by both of these. The salt may be an alkali metal salt or ammonium salt of the acrylic acid, for example. It is preferable that the salt be an alkali metal salt. And it is especially preferable that the salt be a sodium salt. In accordance with use or purpose of the water absorbing agent, an unsaturated monomer other than the acrylic acid and the salt may be contained by 0 to 30 mol %, preferably 0 to 10 mol %, and especially preferably 0 to 5 mol % to the total number of moles of the monomer. Examples of the unsaturated monomer applicable other than the acrylic acid and/or the salt thereof is hydrophilic monomers and salt thereof such as methacrylic acid, (anhydrous) maleic acid, fumaric acid, crotonic acid, itaconic acid, vinylsulfonic acid, 2-(meth)acrylic amide-2-methylpropanesulfonic acid, (meth)acryloxyalkanesulfonic acid, N-vinyl-2-pyrrolidone, N-vinylacetamide, (meth) acrylamide, N-isopropyl(meth)acrylamide, N,N-dimethyl(meth)acrylamide, 2-hydroxyethyl(meth)acrylate, methoxypolyethyleneglycol(meth)acrylate, polyethyleneglycol(meth)acrylate, and the like. The neutralization of the acid group may be carried out while they are still monomer, during and/or after the polymerization.

In the present invention, it is especially preferable for the water absorption that the cross-linking agent be used apart from the unsaturated monomer component other than the acrylic acid and/or the salt thereof. For example, applicable cross-linking agents encompass compounds having at least two polymerizable double bonds such as N,N'-methylenebisacrylamide, (poly)ethyleneglycoldi(meth)acrylate, (poly)prolyleneglycoldi(meth)acrylate, (polyoxyethylene)trimethylolpropanetri(meth)acrylate, trimethylolpropanedi(meth)acrylate, polyethyleneglycoldi($\beta$-acryloyloxypropionate), trimethylolpropanetri($\beta$-acryloyloxypropionate), poly(meth)allyloxyalkane, and the like; and compounds having a covalent bond reactive with a carboxyl group, such as polyglycidylether(ethyleneglycoldiglycidylether and the like), polyalcohol (ethyleneglycol, polyethyleneglycol, glycerin, sorbitol, and the like), and the like. These cross-linking agents may be used solely or in combination. In addition, polyvalent metal compounds such as aluminum sulfate, aluminum hydroxide, calcium sulfate, calcium hydroxide, and zinc oxide are also example of applicable crosslinking agents. In a case where such a polyvalent metal compound is used as an inner cross-linking agent, metal content such as iron, manganese, or copper content is adjusted within a range described below. When a cross-linking agent is used, it is preferable to use a compound having at least two polymerizable double bonds in a molecule in consideration of the water-absorbing property or the like of the resultant water absorbing agent. From a viewpoint of its property, the cross-linking agent is used in a rage of 0.0001 to 5 mol %, preferably 0.005 to 2 mol % to the total number of moles of the monomer.

Moreover, from a viewpoint of the effect of the color stability, the acrylic acid contains a protoanemonin and/or a furfural preferably in a range of 0 to 10 ppm by weight, more preferably in a range of 0 to 5 ppm by weight, and most preferably in a range of 0 to 1 ppm by weight. Furthermore, the acrylic acid used in the present invention may contain an aldehyde other than the furfural and/or maleic acid. It is better that an amount of the aldehyde other than the furfural and/or maleic acid is less in the acrylic acid used in the present invention. The amount of the aldehyde other than the furfural and/or maleic acid is preferably in a range of 0 to 5 ppm by weight, more preferably in a range of 0 to 3 ppm by weight, further more preferably in a range of 0 to 1 ppm by weight, and most preferably in a range of 0 ppm by weight (less than detection limit) to the amount of the acrylic acid. The aldehyde other than the furfural is, for example, benzaldehyde, acrolein, acetaldehyde, or the like.

In the embodiments 1 through 4 of the present invention, especially in the embodiments 3 and 4 of the present invention, from the sake of the color stability, a unsaturated monomer aqueous solution contains iron in a range of 0 to 10 ppm by weight, preferably in a range of 0 to 5 ppm by weight, more preferably in a range of more than 0 to less than 5 ppm by weight, further more preferably in a range of 0.001 to 5 ppm by weight, especially preferably in a range of 0.001 to 4 ppm by weight and most preferably in a range of 0.005 to 3 ppm by weight. The iron is prepared by controlling purity of the alkali metal salt used for neutralization, or the like.

These monomers are usually polymerized in the aqueous solution. A density of its solid content is usually in a range of 10 to 90% by weight, preferably in a range of 20 to 80% by weight, more preferably in a range of 30 to 70% by weight, and most preferably in a range of 40 to 60% by weight. In case where the monomer is polymerized in the aqueous solution, a surface active agent, a polyacrylic acid and/or a salt thereof, a starch, a high polymer compound such as a polyvinyl alcohol or the like, various chelating agents, various additives may be used in combination by a range of 0 to 30% by weight (to the monomers).

(3) Basic Substance

In the manufacturing method of the present invention, in order to obtain the acrylic acid and/or the salt thereof containing the acrylic acid for the neutralization polymerization (the monomer is neutralized in advance) in a range of 1 mol % to 50 mol % and the salt thereof in a range of 50 mol % to 99 mol %, in other words to obtain a neutralizing rate of the acrylic acid in a range of 50 mol % to 99 mol %, the acrylic acid and the salt thereof is preferably prepared by neutralizing an acrylic acid with a basic substance. A hydroxide of an alkaline metal (sodium hydroxide, potassium hydroxide, lithium hydroxide or the like) containing iron in the aforementioned range, a (hydrogen) carbonate (sodium (hydrogen) carbonate, potassium (hydrogen) carbonate), or the like is preferable as the basic substance used for the neutralization so that it is possible to obtain preferably a monovalent salt, more preferably an alkali metal salt or an ammonium salt, especially preferably an alkali metal salt, and sodium hydroxide is particularly preferred. Preferable exemplary conditions for the neutralization process and the like are described in the International Publication WO2006/522181, which may be applied to the present invention.

The first through fourth Embodiments will be described in the following (4) through (8), respectively.

(4) N-oxyl Compound (First Embodiment)

In the First Embodiment of the present invention, the unsaturated monomer includes an N-oxyl compound preferably in a range of 0.01 to 10 ppm by weight, more preferably in a range of 0.1 to 5 ppm by weight, and particularly preferably in a range of 0.1 to 3 ppm by weight. Furthermore, in order to further improve the surface color compared with the ones of the conventional art, the First Embodiment is arranged such that the unsaturated monomer contain a methoxyphenol compound, (for example p-methoxyphenol or di-tert-butylhydroquinone), or conventionally known polymerization inhibitor (e.g., phenothiazine or the like) in a range of 0 to 10 ppm by weight, preferably in a range of 0 to 5 ppm by weight and most preferably by 0 ppm (substantially absent, below detection limits) to the unsaturated monomer content.

In the First Embodiment, in the case the N-oxyl compound is used out of the aforementioned range, the polymerization control is extremely difficult. Since the object of the present invention, that is, a particle-shaped water absorbing agent with the significantly improved surface color while maintaining the high water absorbing property cannot be attained, the usage of the N-oxyl compound out of the range is not preferable.

For example, in the case the unsaturated monomer includes only the methoxyphenol compound of 10 ppm by weight, or in the case the N-oxyl compound is not included at all, the polymerization reaction would take place uncontrollably, thereby causing significant decrease in physical state properties.

The N-oxyl compound used in the present invention is a polymer or a non-polymer compound having one or more N-oxyl structures within its molecule. The N-oxyl compound is preferably a non-polymer compound, particularly a cyclic organic compound, particularly preferably an N-oxyl compound of a piperidine. In addition, the amount of N-oxyl per molecule is preferably 1 to 6, more preferably 1 to 3, and further preferably 1. In addition, the N-oxyl compound has a molecular weight preferably in a range of 50 to 5000, more preferably in a range of 60 to 1000, and particularly preferably in a range of 70 to 800, and the carbon number is preferably in a range of 1 to 500, more preferably in a range of 2 to 100, and particularly preferably in a range of 5 to 50. Specific examples of the N-oxyl compound encompass cyclic organic compounds (particularly piperidines) such as 2,2,6,6-tetramethylpiperidine-1-oxyl, 2,2,6,6-4-hydroxy-tetramethylpiperidine-1-oxyl, 2,2,6,6-tetramethyl-4-oxopiperidine-1-oxyl, 4,4',4"-tris(2,2,6,6-tetrapiperidinoxyl) phosphite and the like. Particularly preferred is 2,2,6,6,-tetrapiperidine-1-oxyl. The N-oxyl compound may be preferably used together with a certain amount of a manganese compound described in the following Second Embodiment. This can further improve the surface color of the water absorbing agent and water absorbing resin.

(5) Manganese Compound (Second Embodiment)

In the Second Embodiment of the present invention, the unsaturated monomer contains a certain amount of methoxyphenol compound and a certain amount of manganese compound.

The amount of methoxyphenol compound used in the Second Embodiment is preferably in a range of 0.01 to 20 ppm by weight, more preferably in a range of 0.1 to 10 ppm by weight, and further preferably in a range of 0.1 to 5 ppm by weight, and most preferably in a range of 0.1 to 3 ppm by weight. In addition, the amount of the manganese compound used in the Second Embodiment is preferably in a range of 0.01 to 10 ppm by weight, more preferably in a range of 0.01 to 5 ppm by weight, further preferably in a range of 0.01 to 2 ppm by weight, and most preferably in a range of 0.1 to 1 ppm by weight (as $MnO_2$).

In the Second Embodiment, in the case the methoxyphenol compound or manganese compound is used out of the aforementioned range, the polymerization control is extremely difficult. Since the object of the present invention, that is, a particle-shaped water absorbing agent with the significantly improved surface color while maintaining the high water absorbing property cannot be attained, the usage of the methoxyphenol compound or the manganese compound out of the range is not preferable.

Examples of the methoxyphenol compound used in the Second Embodiment encompass p-methoxyphenol, t-butyl-catechol, di-t-butylhydroquinone, 3,5-di-t-butyl-4-hydroxytoluene, 3,5-di-t-butyl-4-hydroxytoluene, 2-t-butylphenol, 2-t-butyl-4-methylphenol, 2,5-di-t-butylhydroquinone, 4,6-di-t-butylresordine, 3,6-di-t-butylburentcatechin, 2-t-butyl-resordine, and the like. These methoxyphenol compounds may be used solely or in combination. However, especially preferred is p-methoxyphenol.

The manganese compound used in the Second Embodiment may be an inorganic manganese compound such as manganese permanganate, manganese dioxide, manganese chloride, manganese sulfate, manganese nitrate, particularly an inorganic salt, and more particularly a water-soluble inorganic salt. However from the point of view of the solubility to the solution of the unsaturated monomer and the other factors, the manganese compound is preferably an organic acid salt of manganese, particularly preferably a water-soluble organic acid salt or a water-soluble saturated organic acid salt. The term 'Water-soluble' in the present invention means the solubility of 0.1% or over, further preferably 1% or over, and 10% or over in water at room temperature.

Examples of the manganese organic acid salt favorably applicable in the present invention encompass manganese formate, manganese acetate, manganese octate, manganese dialkyldithiocarbamate (the alkyl group is methyl, ethyl, propyl, or butyl), manganese diphenyldithiocarbamate, and manganese ethylenediamine tetraacetate and the like. The manganese organic acid salts may be used solely or in combination.

In the Second Embodiment, any transition-metal compound other than the aforementioned manganese compound is not preferable in achieving the object of the present invention. For example, a copper compound is conventionally used to control the polymerization control. However, the use of the copper compound is not preferable because it reddens the surface color of the water-absorbing resin acquired after the polymerization (i.e., it increases Hunter a value). Consequently, copper ion content or copper compound content is preferably in a range of 0 to 5 ppm by weight, or more preferably in a range of 0 to 1 ppm by weight, or especially preferably in a range of 0 to 0.3 ppm by weight, or most preferably 0 ppm by weight (as $Cu_2O$).

(6) Polyalkyleneglycol (Third Embodiment)

In the Third Embodiment of the present invention, a polyalkyleneglycol is used. Furthermore, the weight average molecular weight thereof is preferably in a range of 300 to 50000, more preferably in a range of 400 to 30000, and further preferred in a range of 500 to 20000. Note that the term "polyalkyleneglycol" used herein encompasses polyalkylene oxide. The "polyalkyleneglycol" may be a homopolymer constituted by one kind of repeating unit, or may be a block or random copolymer which is constituted by two or more kinds of repeating units. The "polyalkyleneglycol" is a polyoxide or polyglycol whose alkylene unit is C1 (methylene) or greater, preferably C2 (ethylene) to C10 (decane), especially preferably C2 (ethylene) or C3 (propylene), and most preferably C2 (ethylene).

In the Third Embodiment, the desired brightness of the particle-shaped water absorbing agent which is attained when the weight average molecular weight is under 300 cannot be attained, and the effect of preventing the coloring is poor. In addition, in the case the molecular weight of the polyalkyleneglycol exceeds 50000, some method of polymerization has a difficulty in controlling the polymerization temperature due to the increase in viscosity in preparing an aqueous solution of the unsaturated monomer. Therefore, the molecular weight of the polyalkyleneglycol exceeding 50000 is not preferable.

Furthermore, in the Third Embodiment of the present invention, the polyalkyleneglycol is preferably non-radically polymerizable. What is meant by the term 'Non-radical' in the present invention is that the compound has no unsaturated bond in the molecular chain, such as vinyl group or allyl group. If the molecular chain of the polyalkyleneglycol has radically polymerizable unsaturated bond such as the vinyl group or the allyl group, the polymerization reaction of the acrylic acid, which is the unsaturated monomer mainly used in the present invention, would uncontrollably take place depending on which polyalkyleneglycol compound is used. Consequently, the desired absorbing property cannot be attained, and the absorbing property of the particle-shaped water absorbing agent will decrease. Therefore, non-radically polymerizable polyalkyleneglycol is preferable.

The polyalkyleneglycol having one or more of a hydroxyl group in its molecular chain is preferable in the aforementioned polyalkyleneglycols. Examples of the polyalkyleneglycol encompass polyethylene glycol, methoxy-modified polyethylene glycol, polypropylene glycol, methoxy-modified polypropylene glycol, polyoxyethylene arkyl ether and the like, which may be used solely or in combination.

Among the polyalkylene glycols, polyethylene glycol, polypropylene glycol, and polyethylene glycol, polypropylene glycol whose terminal(s) is modified can remarkably achieve the effect of the present invention. Such an alkyleneglycol structure (especially polyethylene glycol) contains the repeating unit per one molecule by 50% or more by weight, preferably 60% or more by weight, especially preferably 80% or more by weight, further especially preferably 90% or more by weight. The most preferred compound is polyethylene glycol, especially unmodified polyethylene glycol.

In order to attain the particle-shaped water absorbing agent of the present invention, the described compounds in the following Japanese Unexamined Patent Publications may also be used as the polyalkyleneglycol used in the present invention: Tokukaisho No. 55-3863, Tokukaisho No. 55-843034, Tokukaisho No. 57-16307, Tokukaihei No. 1-92226, Tokukaihei No. 1-165615, Tokukaihei No. 3-20313, Tokukaihei No. 3-163119, Tokukaihei No. 5-239156, Tokukai No. 2002-26511, and Tokukai No. 2003-51850.

The Third Embodiment of the present invention shows a preferable example of the manufacturing method, in which the polyalkyleneglycol is added to the unsaturated monomer described later. It is preferable to do so in order to remarkably attain the effect of the present invention.

In the Third Embodiment of the present invention, the water-absorbing resin content in the particle-shaped water absorbing agent as its main component is preferably in a range of 70 to 99.9% by weight of the whole particle-shaped water absorbing agent, more preferably in a range of 80 to 99.7% by weight, and further preferably in a range of 90 to 99.5% by weight. The polyalkyleneglycol content is preferably in a range of 0.01 to 10% by weight, more preferably in a range of 0.05 to 5% by weight, and most preferably in a range of 0.1 to 5% by weight.

In the case the content is below the aforementioned usage amount, the desired effect in improving the brightness of the color on the surface of the particle cannot be attained, and if the amount used exceeds the aforementioned range, particularly in the case the polymerization of the unsaturated-monomer aqueous solution is performed by adding and mixing the polyalkyleneglycol with the unsaturated monomer, the control of the polymerization reaction becomes difficult due to the increase in viscosity of the unsaturated-monomer aqueous solution. Thus, it is not preferable to have the water-absorbing resin content or the polyalkyleneglycol content out of the range.

To be uniformly added, the polyalkyleneglycol is prepared as a liquid solution, more specifically, an aqueous solution or an aqueous liquid, and the concentration of the aqueous solution may be around the range of 1 to 50% by weight. Furthermore, a surface-active agent or the like may be used as necessary. The solvent may be dried off as necessary.

In the Third Embodiment of the present invention, as the method of adding or preparing the polyalkyleneglycol and iron, for example, one or a plurality of the following manufacturing steps (a) to (f) for the water-absorbing resin is performed.

Step (a) of preparing an unsaturated-monomer aqueous solution with an acrylic acid and/or the salt thereof as its main component by neutralizing with a basic substance an unsaturated monomer whose main component is the acrylic acid.

Step (b) of performing cross-linking polymerization of the unsaturated-monomer aqueous solution prepared in step (a), by adding a polymerization initiator thereto or irradiating it with an active energy ray such as an ultraviolet ray.

Step (c) of crushing a hydrous gel polymer resultant from the cross-linking polymerization of the unsaturated-monomer aqueous solution including the monomer, and if necessary, neutralizing the hydrous gel polymer with a basic substance as necessary at the same time as the crushing or after the crushing.

Step (d) of obtaining dry powder by, after the steps (a) to (c), drying the hydrous gel polymer, and if necessary crushing the hydrous gel polymer, the dry powder having particles smaller than 150 µm in particle size by 0 to 20% by weight, a mass medium particle size (D50) in a range of 200 µm to 600 µm, and a logarithmic standard deviation ($\sigma\zeta$) in a range of 0.20 to 0.40.

Step (e) of obtaining the water-absorbing resin by surface cross-linking the dried powder obtained in step (d).

Step (f) of adding an additive after the surface cross-linking as necessary.

In order to further enhance the effect of the prevention in coloring of the present invention in these manufacturing methods, polyalkyleneglycol or iron is preferably added or prepared in particular in the step (a) or step (b). Specifically, it is preferable such that the polyalkyleneglycol and iron is added or prepared in the unsaturated-monomer aqueous solution before the polymerization or during the polymerization. The details will be explained later.

In the Third Embodiment of the present invention, it is sufficient that the polyalkyleneglycol is included on the surface or inside of the water-absorbing resin. However from the perspective of the absorbing property and the surface color (brightness) improvement, it is particularly preferable that the polyalkyleneglycol is included evenly in the water-absorbing agent resin.

(7) Iron (First Through Fourth Embodiments, Especially the Third Embodiment)

In the Third Embodiment of the present invention, the particle-shaped water absorbing agent contains iron as an essential constituent, and the method to obtain the iron by iron content in a range of 0.001 to 5 ppm by weight is preferably in the following methods (a) and (b), from the point of view of the polymerization reaction control of the unsaturated monomer.

Method (a) of selecting a basic substance with the iron content in a range of 0.01 to 10 ppm by weight from among commercially-available basic substances (e.g. hydroxide of alkaline metal), and using the basic substance in such an amount as to give the particle-shaped water absorbing agent the iron content of 0.001 to 5 ppm by weight.

Method (b) of removing or reducing the amount of the iron included in a basic compound with iron content of 10 ppm by weight or more with active carbon, chelate ion exchange resin, chelated complex or the like, and adding the iron to iron content of 0.01 to 10 ppm by weight in the particle-shaped water absorbing agent.

In the method (b), the iron may be added to the unsaturated monomer and/or the basic compound. In addition, the iron being used in the method (b) may be a primary salt or a secondary salt such as iron oxide, iron hydroxide, iron sulfate or iron sulfide, and one type or two or more types may be used.

A particle-shaped water absorbing agent of the present invention contains iron preferably in a range of 0.001 to 5 ppm by weight, more preferably in a range of 0.01 to 4 ppm by weight, further more preferably in a range of 0.1 to 4 ppm by weight, and especially preferably in a range of 0.3 to 3 ppm by weight.

It is not preferable that substantially no iron is present. In a case where substantially no iron is present, desired physical properties cannot be obtained since polymerization reaction is affected. Further, iron exceeding the aforementioned range is not preferable because a particle-shaped water absorbing agent is colored.

Note that iron is adjusted within the preferred ranges of materials used in the present invention, an unsaturated-monomer aqueous solution, and the like in accordance with a manufacturing condition so that iron contained in a particle-shaped water absorbing agent is eventually controlled so as to be in the aforementioned range.

Furthermore, the iron content of the particle-shaped water absorbing agent may be attained by adjusting the iron content water-absorbing resin ingredients used other than the basic compound in the methods (a) or (b), such as the unsaturated monomer, water, an inner cross-linking agent, a surface cross-linking agent, or a polyvalent metal compound.

The iron content in the particle-shaped water absorbing agent is controlled from these methods, and is conditioned to the preferred ranges. The specific embodiment of the aforementioned will be described later.

(8) Water-Soluble Thiodialkyl Compound (Fourth Embodiment)

The Fourth Embodiment of the present invention is attained using a water-soluble thiodialkyl compound with a C—S—C constitution in the manufacturing step of the water-absorbing resin and the particle-shaped water absorbing agent.

The water-soluble thiodialkyl compound used in the Fourth Embodiment is a thiodialkyl compound which dissolves 0.1 g or more, preferably 1 g or more, further preferably 10 g or more in 100 g of water of room temperature and normal pressure, and preferably a thiodialkyl compound of a polymer or a non-polymer containing a hydroxyl group or a carboxyl group.

The non-polymer compound has preferably 1 to 10, furthermore 1 to 5, and particularly 1 sulfur atom per molecule, and uses a compound with one or more, preferably 2 to 5 hydroxyl group or carboxyl group per molecule with generally a molecular weight of 50 to 1000, further preferably 100 to 500, or a compound with a carbon number of 2 to 100, further preferably 4 to 50. The molecule may have an unsaturated group, a phenyl group or the like, however particularly from the point of view of the coexistence of the brightness improvement effect in the surface color and the water-absorbing property, saturated alkyl, furthermore saturated (poly or di) hydroxyalkyl, or saturated (poly or di) carboxyalkyl compound is used.

Examples of the water-soluble thiodialkyl compound used in the present invention encompass thiodialkyl alcohols such as 2,2'-thiodiethanol, 1-(2-hydroxyethylthio)-2-propanol, thiodipropyleneglycol, and the like; thiodialkyl acid (carboxylic acid) such as 2,2'-thiodiacetic acid, 2,2'-thiodiglycolic acid, 3,3'-dithiobishydrocinnamic acid, and the like; and salts of these compounds. For better effect, thiodiglycol, thioglycolic acid (in other words, thiodiacetic acid), thiodipropionic acid are more preferable. Moreover, preferable examples of salts of the thiodialkyl acids encompass: alkali metal salts such as sodium salts, potassium salt, and the like; ammonium salts; and amine salts.

The water-soluble thiodialkyl compound is preferably in a range of 0.001 to 10 parts by weight to 100 parts by weight of the water-absorbing resin, more preferably in a range of 0.002 to 1 parts by weight and further preferably in a range of 0.005 to 0.5 parts by weight. If the water-soluble thiodialkyl compound content is below 0.001 parts by weight, there is a possibility that color stability would be low. In addition, if the water-soluble thiodialkyl compound content is more than 10 parts by weight, there are cases where the control of the polymerization becomes difficult, and since the physical property of the particle-shaped water absorbing agent being obtained is unstable, this is not preferable.

The water-soluble thiodialkyl compound of the present invention is added in the manufacturing process of the water-absorbing resin. The water-soluble thiodialkyl compound may be added: in the polymerization monomer solution; during the polymerization reaction; immediately after the polymerization reaction; in the gel-crushing step, after the drying step; immediately before the surface-processing step; in the surface cross-linking agent; after the surface cross-linking step; or the other timing. In order to evenly distribute the water-soluble thiodialkyl compound to the water-absorbing resin, the thiodialkyl compound is preferably added in the polymerization monomer solution or in the gel-crushing step, and is more preferably added in the polymerization monomer solution. The water-soluble thiodialkyl compound may be added as it is, however it is preferable to add the compound as a solution of an aqueous liquid, and is more preferable being added as an aqueous solution. In addition, the concentration range of the water-soluble thiodialkyl compound in the solution is preferably in a range of 0.1 to 90% by weight, more preferably in a range of 0.5 to 50% by weight, and further preferably being in a range of 1 to 20% by weight.

The following descriptions (9) through (20) deal with materials, methods, physical properties, and usages common to the First through Fourth Embodiments of the present invention.

(9) Chelating Agent (Preferably a Water-Soluble Organic Chelating Agent)

The particle-shaped water absorbing agent of the present invention preferably uses a chelating agent in the case the object is to further improve the color stabilization (color stabilization during storage of the particle-shaped water absorbing agent under a condition of high temperature and high humidity for a long term) or the improvement of urinary resistance (preventing the deterioration of the gel).

From the aspect of effectiveness, the chelating agent used is preferably a water-soluble organic chelating agent, and furthermore, is preferably an organic chelating agent which is a non-polymer compound with a nitrogen atom or a phosphorus atom, and more preferably a chelating agent of an aminopolyvalent carboxylic acid type or a chelating agent of an aminopolyvalent phosphoric acid type.

The chelating agent used in the present invention is a compound which gives a metal ion such as a transition-metal ion. Considering the influence towards the polymerization and the physical property of the resultant water absorbing agent, a non-polymer type organic compound with the weight average molecular weight of 5000 or below is preferable, and a non-polymer type organic compound with a molecular weight in a range of 100 to 1000. A molecular weight exceeding 5000 is not preferable, because some polymerization methods would have a difficulty in controlling the polymerization temperature due to the increase in viscosity in preparing an aqueous solution of the unsaturated monomer, if the molecular weight was so high.

A compound with the nitrogen atom or the phosphorus atom is preferable among the aforementioned compounds, and further preferred is an aminopolyvalent carboxylic acid and/or the salt thereof including 2 or 3 or more, preferably 3 to 100, further preferably 3 to 20, and most preferred including 3 to 10 carboxyl groups in its molecule, or a compound of an organic phosphoric acid and/or an salt thereof with a phosphate group.

Examples of the aminopolyvalent carboxylic acid and the salt thereof encompass aminocarboxylic metal chelating agent such as iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid, triethylenetetraaminehexaacetic acid, trans-1,2-diaminocyclohexanetetraacetic acid, bis(2-hydroxyethyl)glycine, diaminopropanoltetraacetic acid, ethylenediamine-2-propionic acid, glycoletherdiaminetetraacetic acid, bis(2-hydroxybenzyl)ethylenediaminediacetic acid, ethylenediaminedisuccinic acid, L-glutamic diacetic acid, 3-hydroxy-2,2'-iminodisuccinic acid, glycoletherdiaminetetraacetic acid, methylglycinediacetic acid, and the salts thereof. These compounds may be used solely or in combination.

One example of the organic phosphoric acid and the salt is hydroxyethylenediphosphoric acid having two phosphoric acid groups in its molecule. Aminopolyvalent phosphoric acids and aminopolyvalent compounds having an amino group, which have three or more phosphoric acid groups in their molecules, are more preferable, and aminopolyvalent phosphoric acids and aminopolyvalent compounds having an amino group, which have three to ten phosphoric acid groups in their molecules, are especially preferable.

Examples of aminopolyvalent phosphoric acids and aminopolyvalent compounds having an amino group, which have three or more phosphoric acid groups in their molecules encompass: ethylenediamine-N,N'-di(methylenephosphinic acid), ethylenediaminetetra(methylenephosphinic acid), nitriloacetic-di(methylenephosphinic acid), nitrilodiacetic-(methylenephosphinic acid), nitriloacetic-β-propionic-methylenephosphonic acid, nitrilotris(methylenephosphonic acid), cyclohyxanediaminetetra(methylenephosphonic acid), ethylenediamine-N,N'-diacetic-N,N'-di(methylenephosphonic acid), ethylenediamine-N,N'-di(methylenephosphonic acid), ethylenediaminetetra(methylenephosphonic acid), polymethylenediaminetetra(methylenephosphonic acid), diethylenetriaminepenta(methylenephosphonic acid), 1-hydroxyethylidenediphosphonic acid, and the salts thereof.

The aminocarboxylic acid and/or the salt thereof having 3 or more carboxyl group, or the organic phosphoric acid and/or the salt thereof may be used solely or two or more types thereof may be used in combination. In addition, alkaline metal salts such as sodium salt or potassium salt, ammonium salts and amine salts are preferable as the salt.

The chelating agent is preferably included in the particle-shaped water absorbing agent in a range of 10 to 5000 ppm by weight, more preferably in a range of 10 to 1000 ppm by weight, further preferably in a range of 50 to 1000 ppm by weight and particularly preferable in a range of 100 to 1000 ppm by weight. If the amount of the chelating agent included is below the aforementioned range, the desired urinary resistance or color stability effect cannot be attained, and if the amount exceeds the range, particularly in the case where the polymerization of the unsaturated-monomer aqueous solution is performed by adding the chelating agent to the unsaturated monomer with stirring, the controlling of the polymerization reaction becomes difficult. Thus, the amount of the chelating agent exceeding the range is not preferable. If the amount of the chelating agent included is below the range, the desired urinary resistance or color stability effect cannot be attained, and if the amount exceeds the range, particularly in the case the chelating agent is added to the water-absorbing resin, the decrease in absorption property (absorbency, water soluble content) and decrease in surface tension occurs. Thus, the amount of the chelating agent exceeding the range is not preferable.

An example of a favorable manufacturing method for producing the particle-shaped water absorbing agent of the present invention is such that the chelating agent is to be preferably added to the unsaturated-monomer aqueous solution with the acrylic acid as its main component. This attains a remarkable effect of the present invention.

(10) Hydroxy-Carboxylic Compound

Furthermore, for the effect of color stability, the monomer or the polymer prepared therefrom may have a hydroxyl-carboxylic compound or the like such as a lactic acid and/or the salt thereof, a citric acid and/or the salt thereof and a malic acid and/or the salt thereof, especially non-polymer hydroxyl carboxylic acid and/or the salt thereof, as described in the International Application WO2007/JP/67348 (International Application date: Aug. 30, 2007).

The hydroxyl-carboxylic compound is preferably added in a range of 1 to 100000 ppm by weight with respect to the monomer, or in a range of 1 to 10000 ppm by weight with respect to the solid content of the water-absorbing resin, for the sake of cost performance.

(11) Preparation of the Unsaturated-Monomer Aqueous Solution

In the case a reverse-phased suspension polymerization or an aqueous solution polymerization is performed in the polymerization step of the First through Fourth Embodiments of the present invention, an aqueous solution of the unsaturated monomer is prepared (if necessary the solution contains an inner cross-linking agent), and the unsaturated monomer content in this aqueous solution (hereafter referred to as monomer aqueous solution) is preferably in a range of 10 to 70% by weight, more preferably in a range of 15 to 65% by weight, further preferably in a range of 30 to 65% by weight, particularly preferably in a range of 30 to 60% by weight, and most preferably in a range of 35 to 55% by weight, from the physical property point of view. A solvent other than water may also be used in combination as necessary, and the type of solvent used in combination is not particularly limited.

In the First to Fourth Embodiment of the present invention, the particular compound preferably exists in the stage of preparing the unsaturated-monomer aqueous solution, in order that the particular compound may be evenly distributed in the water-absorbing resin and the particle-shaped water absorbing agent.

Specifically, in the First Embodiment of the present invention, the unsaturated-monomer aqueous solution thus prepared contains the N-oxyl compound in the aforementioned range preferably.

In the Second Embodiment of the present invention, the unsaturated-monomer aqueous solution thus prepared contains the manganese compound in the aforementioned range preferably.

In the Third Embodiment of the present invention, as an example of the manufacturing method, in the case the polyalkyleneglycol or iron is mixed in the monomer aqueous solution, the mixing method is not particularly limited, however is preferably to add and the polyalkyleneglycol or iron to the monomer or the monomer aqueous solution with stirring, before preparing the unsaturated-monomer aqueous solution.

In addition, as an example of a manufacturing method in the Third Embodiment, the addition of the iron into the monomer aqueous solution is carried out preferably at neutralizing the unsaturated-monomer aqueous solution with the basic substance.

In the Third Embodiment, the unsaturated-monomer aqueous solution contains iron in a range of 0.01 to 10 ppm by weight, preferably in a range of 0.01 to 5 ppm by weight, and more preferably 0.01 to 3 ppm by weight. Note that, also in the First Embodiment, the Second Embodiment, and the Fourth Embodiment, the unsaturated-monomer aqueous solution contains iron in the aforementioned range.

In the Fourth Embodiment of the present invention, the water-soluble thiodialkyl compound is preferably contained in an amount within the aforementioned range.

Furthermore, the unsaturated-monomer aqueous solution may be improved in various physical properties of the water-absorbing resin or the particle-shaped water absorbing agent by adding to the monomer (i) a water-soluble resin or a water-absorbing resin such as starch, polyacrylic acid and/or the salt thereof, or polyethyleneimine, for example in a range of 0 to 50% by weight, preferably in a range of 0 to 20% by weight, particularly preferably in a range of 0 to 10% by weight, and most preferably in a range of 0 to 3% by weight, or (ii) various foaming agents (a carbonate, an azo compound, a bubble or the like), a surface-active agent or an additive explained later, for example in a range of 0 to 5% by weight, and preferably in a range of 0 to 1% by weight.

(12) Polymerization Step (Cross-Linked Polymerization Step)

From the aspect of the performance and from the ease in controlling of the polymerization, the method for polymerization is usually performed by an aqueous solution polymerization or a reverse-phased suspension polymerization, particularly an aqueous solution polymerization which is conventionally difficult to control its polymerization and improve the coloring. Furthermore, the aqueous solution polymerization may be carried out continuously. Particularly, continuous polymerization in which an unsaturated monomer aqueous solution is polymerized so that a hydrous gel polymer is produced in huge scale at 0.5 t/day or more per line, further 1 t/day or more per line, moreover 5 t/day or more per line, particularly 10 t/day or more per line can be controlled excellently. A continuous kneader polymerization and a continuous belt polymerization are examples of a favorable continuous polymerization. The continuous polymerization is preferably carried out in such a manner that the polymerization is initialized at high temperatures (30° C. or higher, furthermore 40° C. or higher) with high monomer concentration (30% or higher by weight, particularly 40% or higher by weight). When the method of the present invention includes such a polymerization method or polymerization process, the method of the present invention allows the particle-shaped water absorbing agent to have improved coloring and the water-absorbing property at the same time.

These polymerizations may be performed under air atmosphere, however from the point of coloring improvement, the polymerization is preferably performed in an inert gas atmosphere (for example, oxygen concentration 1% or less) such as nitrogen and argon. In addition, the monomer constituent is preferably used for the polymerization after the dissolved oxygen in the monomer or in a solution containing the monomer is sufficiently replaced with the inert gas (for example, oxygen less than 1 ppm).

The evaporating water and acrylic acid during the polymerization is preferably collected and kept as necessary, and further recycled in the manufacturing step of the water-absorbing resin.

The reverse-phased suspension polymerization is a method for polymerization suspending the monomer aqueous solution in a hydrophobic organic solvent, and is described in the following U.S. patents, for example U.S. Pat. Nos. 4,093,776, 4,367,323, 4,446,261, 4,683,274, and 5,244,735 and the like. The aqueous solution polymerization is a method for polymerizing the monomer aqueous solution without using a dispersion solvent, and is described in the following U.S. patents, for example U.S. Pat. Nos. 4,625,001, 4,873,299, 4,286,082, 4,973,632, 4,985,518, 5,124,416, 5,250,640, 5,264,495, 5,145,906, 5,380,808 and the like, and also in European patents such as European Patent No. 0811636, No. 0955086, No. 0922717, No. 1178059 and the like. The monomers, cross-linking agents, polymerization initiators, and other additives each of which are described on these patents are also usable in the polymerization of the present invention.

The polymerization initiator for use in the present invention is selected as appropriate, depending on how the polymerization is carried out. Examples of the polymerization initiators encompass photodegradable polymerization initiator, heat degradable polymerization initiator, redox-type polymerization initiator, and the like. Example of the photodegradable polymerization initiator encompass benzoin derivative, benzyl derivative, acetophenone derivative, benzophenone derivative, azo compounds, and the other. Examples of the heat degradable polymerization initiator encompass: persulfate salts such as sodium persulfate, potassium persulfate, ammonium persulfate; peroxides such as hydrogen peroxide, t-butylperoxide, methylethylketoneperoxide; azo compounds such as azonitrile compound, azoamidine compound, cyclic azoamidine compound, azoamide compound, alkylazo compound, 2,2'-azobis(2-amidinopropane)dihydrochloride, 2,2'-azobis[2-(2-imidazoline-2-il)propane]dihydrochloride, and the like. Examples of the redox-type polymerization initiator encompass a combinational use of the persulfate salt or peroxide, and a reducing compound such as L-ascorbic acid or sodium hydrogen sulfite. In the present invention, combinational use of the photodegradable polymerization initiator and the heat degradable polymerization initiator is also preferable. The polymerization initiator is used in a range of 0.0001 to 1 mol %, and preferably in a range of 0.001 to 0.5 mol % with respect to the amount in the monomer.

(13) Gel Particle Refining Step

The hydrous gel polymer obtained from the polymerization (hydrous gel-form cross-linked polymer, hereafter referred as hydrous gel) may be dried as it is, however may be crushed using a crushing machine as necessary, and is made into particles. The temperature of the hydrous gel when crushing is insulated or heated preferably in a range of 40 to 95° C., and further preferably in a range of 50 to 80° C., from the aspect of physical property when the gel is crushed.

The solid resin content of the hydrous gel is not particularly limited, however is preferably in a range of 10 to 70% by weight, more preferably in a range of 15 to 65% by weight, and further preferable in a range of 30 to 55% by weight from the aspect of physical property.

The gel crushing is performed while polymerizing or after the polymerization, and is possible to preferably crush by extruding the gel from the continuous kneader or a porous structure of a pore size between 0.3 to 30 mm, more preferably between 5 to 30 mm, and further preferably between 5 to 20 mm. The shape of the pore is not particularly limited and may be round, quadrangle such as a square or a rectangle, triangular or hexagonal. However, the gel is preferably extruded from a round-shaped pore. The pore size may be stipulated from the diameter of the circle, the circumference of the open section being calculated as the circumference of the circle.

If the pore size of the porous structure is smaller than 0.3 mm, the gel may become a string-shape, or there is a possibility that the gel cannot be extruded. If the pore size of the porous structure is bigger than 30 mm, the drying of the hydrous gel becomes insufficient, thus the effect of the present invention may not be obtained.

A crushing extruding machine, which can send the hydrous gel from its inlet to a porous die while applying pressure, is used. For example, extruders of a screw type or a rotating roll type are applicable. A screw-type extruder may have one screw or multiple screws, and may be a machine usually used for extruding meat, rubber or plastic, or may be a machine used as a crusher. For example, a meat chopper or a dome granulator may be used.

The crushing and extrusion using such a machine may be carried out together with water, a polyhydric alcohol, a mixture of water and the polyhydric alcohol, a solution or the vapor thereof of a polyvalent metal, or the like.

The polyalkyleneglycol may be mixed in when granulating (segmenting) the hydrous gel in the Third Embodiment of the present invention.

Furthermore, the change in color can be further reduced by adding the chelating agent or the hydroxyl-carboxylic compound in a form of an aqueous solution within the aforementioned ranges, when crushing the gel by extrusion.

(14) Drying Step

In order to attain the reduction of residual monomers, the prevention of deterioration of the gel (urinary resistance) and the prevention of yellowing which are objects of the present invention including the First through Fourth Embodiments, it is preferable that the time between start of the drying of the gel and end the polymerization (if necessary, the gel crushing step therebetween) is as short as possible. Specifically, the drying of the hydrous gel-form cross-linked polymer thus prepared via the polymerization preferably starts (putting the hydrous gel-form cross-linked polymer in a dryer) within 1 hour, more preferably within 0.5 hour, and further preferably within 0.1 hour from the polymerization. In addition, in order to attain the reduction of the residual monomer and reduction of coloring, the temperature of the hydrous gel-form cross-linked polymer from the end of the polymerization to the start of drying is controlled preferably in a range of 50 to 80° C., and further preferably in a range of 60 to 70° C.

A dried product is obtained by drying the hydrous gel-form cross-linked polymer to solid resin content of preferably 80% or more by weight, more preferably 85 to 99% by weight, further preferably 90 to 98% by weight, and particularly preferably 92 to 97% by weight. The solid resin content can be worked out from drying loss (worked out by heating 1 g of powder or particles for 3 hours at 180° C.). The drying temperature is not particularly limited, however is preferably in a range of 100 to 300° C., and more preferably in a range of 150 to 250° C. Various methods are applicable as the drying method, such as drying by heating, hot-air drying, vacuum drying, infrared drying, microwave drying, drum dryer drying, dehydration effected by an azeotrope with a hydrophobic organic solvent, and a high humidity drying utilizing steam of high temperature. Preferably, the hot-air drying is performed with a gas of a dew-point temperature in a range of 40 to 100° C., and more preferably with a gas of a dew-point temperature in a range of 50 to 90° C.

(15) Crushing and Classification Step (Particle Size and Conditioning after Drying)

After the step of drying the hydrous gel-form cross-linked polymer, the particle size thereof may be adjusted after the drying as necessary. In order to improve the physical property in the surface cross-linking described later, the particles are preferably made into a certain particle size. The particle size can be appropriately adjusted by polymerization (particularly reverse-phased suspension polymerization), crushing, classification, granulation, dust collection or the like.

The mass medium particle size (D50) before the surface cross-linking is adjusted to be in a range of 200 to 600 μm, preferably in a range of 200 to 550 μm, more preferably in a range of 250 to 500 μm, and particularly preferably in a range of 350 to 450 μm. In addition, a smaller amount of the particles less than 150 μm in diameter is preferable, and the amount is adjusted to be usually in a range of 0 to 5% by weight, preferably in a range of 0 to 3% by weight, and particularly preferably in a range of 0 to 1% by weight. Furthermore, a smaller amount of the particles of 850 μm and over is preferably, and the amount is adjusted to be usually in a range of 0 to 5% by weight, preferably in a range of 0 to 3% by weight, and particularly preferred in a range of 0 to 1% by weight. The logarithmic standard deviation of the particle distribution (σζ) is preferably in a range of 0.20 to 0.40, more preferably in a range of 0.27 to 0.37, and particularly preferable in a range of 0.25 to 0.35.

The method of these is described in for example the International Application No. WO2004/69915.

(16) Surface Cross-Linking Step

A water-absorbing resin particle obtained in the present invention may be made a water-absorbing resin suitable as a raw material for sanitary goods by going through a conventionally known surface cross-linking processing step. The surface cross-linking is to provide on the surface layer of the water-absorbing resin (vicinity of surface: usually a layer of around several 10 μm from the surface of the water-absorbing resin surface) a section with a further higher cross-linking density. The surface cross-linking can be done by radical cross-linking reaction on the surface, surface cross-linking polymerization, cross-linking reaction with a surface cross-linking agent or the like.

Various organic or inorganic cross-linking agents may be given as examples for the surface cross-linking agent that may be used for the present invention, however from the point of physical property and the easiness of handling, a cross-linking agent which can react with carboxyl group is preferably used. For example, a polyhydric alcohol compound, an epoxy compound, a polyvalent amine compound or a product of condensing the polyvalent amine compound with a haloepoxy compound, an oxazoline compound, a mono, di or poly oxazolidinon compound, a polyvalent metal salt, an alkylene carbonate compound or the like may be given as examples.

More specifically, the compounds listed in U.S. Pat. Nos. 6,228,930, 6,071,976, 6,254,990, and the like are examples. For example, polyvalent alcohol compounds such as mono, di, tri, tetra, or poly ethyleneglycol, monopropyleneglycol, 1,3-propanediol, dipropyleneglycol, 2,3,4-trimethyl-1,3-pentanediol, polypropyleneglycol, glycerin, polyglycerin, 2-butene-1,4-diol, 1,4-butanediol, 1,3-butanediol, 1,5-pentanediol, 1,6-hexanediol, 1,2-cyclohexanedimethanol, and the like; epoxy compounds such as ethyleneglycoldigricidylether, glycidol, and the like; polyvalent amine compounds such as ethylenediamine, diethylenetriamine, triethylenetetramine, tetraethylenepentamine, pentaethylenehexamine, polyethyleneimine, polyamidepolyamine, and the like; haloepoxyl compounds such as epichlorohydrin, epibromhydrin, α-methylepichlorohydrin, and the like; condensed compounds of the polyvalent amine compound and the haloepoxy compound; oxazolidinone compounds such as 2-oxazolidinone and the like; alkylene carbonate compounds such as ethylene carbonate and the like; oxetane compounds; cyclic urea compounds such as 2-imidazolidinone; and the like. It should be noted that the present invention is not limited to these compounds.

The amount of the cross-linking agent used depends on the compound or the combination of the compounds to be used. To 100 parts by weight of the water-absorbing resin particle, the amount of the cross-linking agent used is preferably in a range of 0.001 to 10 parts by weight, and is more preferably in a range of 0.01 to 5 parts by weight. In the present invention, together with the surface cross-linking agent, water may also be used. The amount of water used therewith is preferably in a range of 0.5 to 20 parts by weight to 100 parts by weight of the water-absorbing resin particle, and is more preferably in a range of 0.5 to 10 parts by weight. In addition, a hydrophilic organic solvent may be used in the present invention, apart from water.

The hydrophilic organic solvent can be used, and an amount of the hydrophilic organic solvent therewith is in a range of 0 to 10 parts by weight to 100 parts by weight of the water-absorbing resin, and is preferably in a range of 0 to 5 parts by weight. In addition, in mixing the cross-linking agent solution with the water-absorbing resin particle, a water-insoluble fine particle powder or a surface active agent may coexist therein within such a range that does not disturbs the effect of the present invention, for example in a range of 0 to 10% by weight, preferably in a range of 0 to 5% by weight, and more preferably in a range of 0 to 1% by weight. The surface active agent and its amount that is used is illustrated in the International Application, No. WO2005JP1689 (International application date: Feb. 4, 2005).

Various mixing machines may be used as the mixing device used in mixing the cross-linking agent solution, however a high-speed stirring type mixer, particularly a high-speed stirring type continuous mixer is preferable, such as product name Turbulizer (manufactured by Hosokawa Micron Corporation, Japan), product name Loedige mixer (manufactured by Loedige, Germany) or the like.

The water-absorbing resin after being mixed with the surface cross-linking agent is preferably heat processed, and is cooling processed after the heat processing as necessary. The heating temperature is in a range of 70 to 300° C., preferably in a range of 120 to 250° C., and more preferably in a range of 150 to 250° C. The heating time is preferably in a range of 1 minute to 2 hours. The heat processing may be performed using a normal drier or a heating furnace. The present invention provides a highly white water-absorbing resin even if the water-absorbing resin is subjected to drying with high temperature heat application or air (hot air), each of which conventionally causes severe coloring.

The method for the surface cross-linking process is also described in the following published patents: European Patents No. 0349240, No. 0605150, No. 0450923, No. 0812873, No. 0450924, No. 0668080 and the like, Japanese Patent Application Publications Tokukaihei No. 7-242709, No. 7-224304 and the like, U.S. Pat. Nos. 5,409,771, 5,597,873, 5,385,983, 5,610,220, 5,633,316, 5,674,633, 5,462,972 and the like, and International Publications No. WO99/42494, No. WO99/43720, No. WO99/42496 and the like. The surface cross-linking methods described in these publications may also be applied to the present invention. In addition, in the surface cross-linking processing step, a water-soluble polyvalent metal salt may further be added after the crosslinking reaction, such as an aluminum sulfate aqueous solution. The method for this is described in the International Applications No. WO2004/69915, No. WO2004/69293 and the like, and these also may be applied to the present invention.

(17) Other Steps

Other than the aforementioned steps, a granulation step, a fine particle removing step, a fine particle recycling step or the like may be provided as necessary. Furthermore, in order to gain the effect of long-term color stability, the prevention of the deterioration of gel and the like, the additive described later may be used for the monomer or its polymer.

(18) Particle-Shaped Water Absorbing Agent and its Property

The present invention provides a novel particle-shaped water absorbing agent due to the aforementioned preferable attainment mean of the First through Fourth Embodiments of the present invention. Specifically, the water-absorbing property (absorbing rate, soluble amount, residual monomer amount) and the improvement in whiteness coexist in the particle-shaped water absorbing agent. For example, the particle-shaped water absorbing agent has a good balance in the AAP, GVs, water-soluble amount and the residual monomer amount desired from a sanitary supply, has high physical property, and also has the effect of coloring prevention such as the improvement of the surface color (whiteness improvement).

The particle-shaped water absorbing agent of the present invention contains the polyacrylic acid and/or the salt thereof as the main component, and a b value in the Hunter Lab color scale of the particle is preferably in a range of −5 to 10, more preferably in a range of −5 to 5, further preferably in a range of −4 to 4, particularly preferably in a range of −3 to 3, particularly further preferably in a range of −0.5 to 3, and most preferably in a range of 0 to 3. Furthermore, in the Hunter Lab color scale measurement by the spectral color difference meter, the particle-shaped water absorbing agent of the present invention preferably has an L value (Lightness) of at least 85, further in a range of 90 to 100, preferably in a range of 91 to 100 or 92 to 100, and most preferably in a range of 95 to 100. In addition, an a value is in a range of −2 to 2, at least in a range of −1 to 1, preferably in a range of −0.5 to 1, and most preferably in a range of 0 to 1.

Regarding the Lab values, one or more of the aforementioned preferable ranges should be satisfied. Preferably two or more of the aforementioned preferable ranges of L/a/b should be satisfied. It is particularly preferable that the L value be in a range of 90 to 100, the a value be in a range of −1 to 1, and the b value be in a range of −3 to 3. It is the most preferable that the L value be in a range of 90 to 100, the a value be in a range of 0 to 1, and the b value be in a range of 0 to 3.

Furthermore, the water-absorbing resin shows the L value (Lightness) of at least 70, further in a range of 74 to 100, preferably in a range of 78 to 100, particularly preferably in a range of 80 to 100. The L value here is the L value in the Hunter Lab color scale measurement from the spectral color difference meter of the particle after being exposed in an atmosphere of a temperature in a range of 69 to 71° C. with a respective humidity in a range of 64 to 66%. (The maximum amount of the L value is usually 100, however if the particle exposed under this condition shows 70 or more, practically no problem occurs in color stability).

In addition, the particle-shaped water absorbing agent has a CPI in a range of 1 to 100, preferably in a range of 1 to 50, further preferably in a range of 1 to 30, more further preferably in a range of 1 to 20, particularly preferably in a range of 1 to 10, more particularly preferably in a range of 2 to 10, and most preferred in a range of 3 to 10.

In addition, the particle-shaped water absorbing agent preferably satisfies at least one of the following (a) to (c):

(a) the particle-shaped water absorbing agent contains particles smaller than 150 μm in particle size by 0 to 5% by weight, and has a mass medium particle size (D50) in a range of 200 to 600 μm and a logarithmic standard deviation (σζ) of particle size distribution in a range of 0.20 to 0.40;

(b) the particle-shaped water absorbing agent has an AAP of 20 g/g or more for 0.90 wt % saline under pressure of 1.9 kPa or 4.8 kPa for 60 min; and (c) the particle-shaped water absorbing agent has SFC of 5 ($cm^3$s $10^{-7}$/g) or more for 0.69 wt % saline.

In the First Embodiment being a preferable attainment mean, the particle-shaped water absorbing agent is a particle-shaped water-absorbing resin with the acrylic acid and/or the salt thereof as the main component, essentially including the N-oxyl compound, and satisfying the above.

In the preferable Second Embodiment, the particle-shaped water absorbing agent is a particle-shaped water-absorbing resin with the acrylic acid and/or the salt thereof as the main component, includes the manganese compound, and satisfies the above.

In the preferable Third Embodiment, the present invention is a particle-shaped water absorbing agent including a water-absorbing resin in the type of a polyacrylic acid and/or the salt thereof and polyalkyleneglycol or Fe, and satisfying the above.

In addition, the polyalkyleneglycol or Fe only had to exist in either the surface or the inside of the particle-shaped water absorbing agent, however from the water-absorbing property and the surface color (whiteness) improvement point of view, the polyalkyleneglycol or Fe is particularly preferable being included in uniform in the particle-shaped water absorbing agent.

In the preferable Fourth Embodiment, the particle-shaped water absorbing agent includes the water-absorbing resin in the type of polyacrylic acid and/or the salt thereof or a water-soluble thiodialkyl compound, and satisfies the above. The water-soluble thiodialkyl compound is included in the surface or the inside of the water absorbing agent, however is preferably included in the inside, furthermore in the inside in uniform.

Furthermore, in the First to Fourth Embodiment, the chelating agent is preferably included in order to improve the color stability of the particle-shaped water absorbing agent in the course of time.

The particle-shaped water absorbing agent in the present invention is an absorbing gelatinizing agent for an aqueous liquid (another name: solidifying agent), and is used for absorbing urine, particularly human urine, however if water in a solid state, liquid state and a gas state is included as an aqueous solution, it is not particularly not limited to water itself or a water mixture.

Note that color and other physical properties of a water-absorbing agent or a water-absorbing resin of the present invention are defined by color obtained in an unused state and before subjected to absorption gelatinization (e.g., powder itself or powder in a compound). That is, in a case where a powdery water absorbing resin (water absorbing agent) is manufactured and sold, or can be obtained, color and other physical properties can be measured from the powdery water absorbing resin itself. Further, in a case where a powdery water absorbing resin is compounded with other materials (e.g. pulp) in a diaper, a sanitary napkin, or the like, powder is separated from the other materials so that color and other physical properties can be measured. In this case, water contained in the powder is adjusted so as to be in a predetermined range (e.g. 10% or less by weight, or in a range of 4 to 6% by weight) if necessary.

Further, even immediately after manufacture of a water absorbing agent (or water absorbing resin), even before shipment from a factory, or even after manufacture of sanitary materials, color of a particle-shaped water absorbing agent or water absorbing resin of the present invention can be measured from an unused one contained in a sealed (unopened) packaging material such as polyethylene, or a container, or can be measured from one extracted from an unused sanitary material or the like.

Note that, in a case where the particle-shaped water absorbing agent (or water absorbing resin) extracted from the unused sanitary material contains water of more than 10% by weight, it is preferable that color is measured after the particle-shaped water absorbing agent (or water absorbing resin) is subjected to vacuum drying under temperature which does not affect physical properties (e.g. room temperature) so as to contain water of 10% by weight, or preferably in a range of 4 to 6% by weight.

Further, color can be obtained as a hunter whiteness value (L, a, b) described in JISZ8719 (established in 1970, and revised in 2004).

In the following, the properties of the present invention are explained.

(a) Particle Size

A particle size of the particle-shaped water absorbing agent of the present invention is controlled so as to be adjusted to one of the preferable specific particle sizes below. Crushing, classification, agglomeration, collection of fine powder, etc. are performed in order to obtain one of the preferable particle sizes.

A weight-average particle diameter (D50) of the particle-shaped water absorbing agent is in a range of 200 to 600 μm, preferably in a range of 250 to 550 μm, more preferably in a range of 200 to 500 μm, or most preferably in a range of 350 to 450 μm. Fewer particles smaller than 150 μm are better. Such particles are adjusted so as to be in a range of, normally, 0 to 5% by weight, preferably in a range of 0 to 3% by weight, or most preferably in a range of 0 to 1% by weight. In addition, fewer particles larger than 850 μm are better. Such particles are adjusted so as to be in a range of, normally 0 to 5% by weight, preferably in a range of 0 to 3% by weight, or most preferably in a range of 0 to 1% by weight. A logarithmic standard deviation (σξ) of the particle size distribution is in a range of, preferably, 0.20 to 0.40, more preferably in a range of 0.27 to 0.37, or most preferably in a range of 0.25 to 0.35.

An effect of absorbing goods based on the particle-shaped water absorbing agent such as paper diapers is low in a case where the particle size distribution is out of these ranges.

A bulk density (prescribed in JIS K-3362) is adjusted so as to be in a range of, preferably, 0.40 to 0.90 g/ml or more preferably in a range of 0.50 to 0.80 g/ml. Particles whose weight average particle size is between 150 and 600 μm account for, preferably, from 60 to 100% by weight, more preferably from 70 to 100% by weight, or most preferably from 80 to 100% by weight in the whole particles.

(b) Absorption Under Load (Absorbency Against Pressure (AAP))

With the surface cross-linking as a means for realization of the particle-shaped water absorbing agent, the absorbency against pressure (AAP) thereof for 0.9 wt % saline under pressure of 1.9 kPa or 4.8 kPa applied thereon is controlled so as to be preferably 20 g/g or more or more preferably 25 g/g or more. In a case where the AAP under pressure of 1.9 kPa or 4.8 kPa is less than 20 g/g, much liquid returns, the so-called "re-wet" arises when the particle-shaped water absorbing agent is used for a diaper. This re-wet is undesirable because an infant may suffer from a diaper rash thereby. Although there is no upper limit, the AAP is normally 60 g/g in consideration of balance with other characteristics and cost.

(c) Saline Flow Conductivity (SFC) for 0.69 Wt % Saline

With the surface cross-linking as a means for realization of the particle-shaped water absorbing agent, the saline flow conductivity thereof for 0.69 wt % saline (prescribed in WO2004/069915), which is a liquid permeability under pressure, is controlled so as to be 1 ($cm^3 \cdot s \cdot 10^{-7}/g$) or more, preferably 10 ($cm^3 \cdot s \cdot 10^{-7}/g$) or more, more preferably 50 ($cm^3 \cdot s \cdot 10^{-7}/g$) or more, much more preferably 70 ($cm^3 \cdot s \cdot 10^{-7}/g$) or more, or most preferably 100 ($cm^3 \cdot s \cdot 10^{-7}/g$) or more.

(d) Surface Color of the Particle-Shaped Water Absorbing Agent

The particle-shaped water absorbing agent of the present invention is suitable for hygienic goods such as paper diapers and keeps a significantly white color with clean sensation. That is, a high whiteness of the surface color of the particle-shaped water absorbing agent gives a high sensation of cleanness when the particle-shaped water absorbing agent is used for absorbing goods. A preferable surface color of the particle-shaped water absorbing agent determined through the manufacturing process above has the Hunter L value, the Hunter a value, and the Hunter b value within the ranges above. The preferable color is a significantly clean white.

(e) Gel Volume in Saline (GVs)

With the polymerization as a means for realization of the particle-shaped water absorbing agent, the gel volume in saline (GVs) thereof is controlled so as to be preferably 10 g/g or more, more preferably 20 g/g or more, much more preferably 25 g/g or more, or most preferably 30 g/g or more. Although a higher GVs is preferable and there is no upper limit thereof, in consideration of balance with other characteristics, the GVs is preferably less than 50 g/g, more preferably less than 45 g/g, or most preferably less than 40 g/g.

The particle-shaped water absorbing agent having the GVs of less than 10 g/g is not suitable for hygienic goods such as diapers because an absorbed content is too small. In a case where the GVs is higher than 50 g/g, there is a risk that a water absorbing agent having an excellent liquid permeability cannot be obtained and the gel strength thereof is low.

(f) Water-Soluble Content

With the polymerization as a means for realization of the particle-shaped water absorbing agent, the water-soluble content thereof is preferably less than 35% by weight, more preferably less than 25% by weight, further preferably less than 15%, or most preferably less than 10% by weight. In a case where the water-soluble content is more than 35% by weight, the liquid permeability of the particle-shaped water absorbing agent and the gel strength thereof would be low. Also, in a case where the particle-shaped water absorbing agent is used inside a diaper for a long time, absorbencies (GVs, AAP, etc.) would decrease with time.

(g) Residual Monomer

With the polymerization as a means for realization of the particle-shaped water absorbing agent, the residual monomer content is preferably less than 400 ppm by weight, more preferably less than 300 ppm by weight, or most preferably less than 200 ppm by weight.

(h) GEX Value

GEX value is defined by an equation below where y (g/g) represents the gel volume in saline (GVs value) and x (% by weight) represents the water-soluble content. The GEX value is to express, with one value, an evaluation such that less water-soluble content to the GVs value is better and more water-soluble content to the GVs value is worse. The higher the GEX value is, the higher the performance of the water absorbing agent is. In consideration of balance with other characteristics (AAP, a liquid permeability under pressure, etc.) and productivity, the GEX value is controlled so as to be in a range of 15 to 60, preferably in a range of 18 to 50, or most preferably in a range of 18 to 30.

$$GEX\ value=(y+17)/\ln(x), x>1 \quad \text{Equation 1:}$$

ln (x): natural logarithm of x
The GEX value is represented by:

$$GEX\ value=y/x \quad \text{Equation 2:}$$

where x<1.

With the polymerization as a means for realization of the particle-shaped water absorbing agent, the GEX value is preferably more than 18 or more preferably more than 20.

(i) Cross-Linked Polymer Property Index: CPI

A cross-linked polymer property index (CPI) is defined by an equation below. The CPI is to express, with one value, an evaluation such that less residual monomer to the GEX value is better and more residual monomer to the GEX value is poorer regarding relation between the residual monomer content (ppm by weight) and the GEX value representing the relation of y (g/g): the gel volume in saline (GVs value) and x (% by weight): the water-soluble content.

$$CPI=(GEX/z)\times 100\ (z\ \text{is residual monomer (ppm by weight)}) \quad \text{Equation 3:}$$

In a case where the residual monomer content is less than 20 ppm by weight, the CPI is defined by an equation below.

$$CPI=GEX-z \quad \text{Equation 4:}$$

Although a higher CPI is preferable and there is no upper limit thereof, in view of balance with other characteristics (AAP, a liquid permeability under pressure, etc.) and productivity, the CPI is in a range of 1 to 100, preferably in a range of 1 to 50, more preferably in a range of 1 to 30, further more preferably in a range of 1 to 20, especially preferably in a range of 1 to 10, more especially preferably in a range of 2 to 10, or most preferably in a range of 3 to 10.

The CPI which is out of these ranges is undesirable because disruption of the balance of the liquid permeability under pressure etc. such as the SFC may occur.

(19) Other Additives

In order to add various functions according to functions of objects, the particle-shaped water absorbing agent may be arranged such that the water-absorbing resin thereof is added an additive such as: organic acids, an oxidant, a reductant such as a (hydrogen) sulfite salt, a multivalent metal compound in pamphlets of international publication No. 2004/69915, 2004/113452, 2005/108472, a water-insoluble inorganic or organic powder such as silica, a metal soap, etc., a deodorant, an anti-bacterial agent, a polymeric polyamine, a pulp, a thermoplastic fiber, or the like. An amount of the additive to add is in a range of 0 to 3% by weight or preferably in a range of 0 to 1% by weight.

(20) Usage

Although a usage of the particle-shaped water absorbing agent is not specifically limited, the particle-shaped water absorbing agent is preferably used in absorbing goods such as paper diapers, sanitary napkins, incontinent pads, and the like. Specifically, the particle-shaped water absorbing agent is used in high-concentration diapers each of which contains a large amount of water absorbing resin and conventionally has problems such as odor and coloring deriving from raw materials of the particle-shaped water absorbing agent. The particle-shaped water absorbing agent shows excellent capability especially in a case where the water absorbing agent is used in the absorbing material of the upper layers of the absorbing goods.

The absorbing goods of the present invention are the particle-shaped water absorbing agent, an absorbing material obtained by, according to need, forming hydrophilic fibers into a shape of a sheet, and absorbing goods having a surface sheet with the liquid permeability and a back sheet with a liquid impermeability. The absorbing material without the use of the hydrophilic fibers is made by fixing the particle-shaped water absorbing agent on a paper and/or nonwoven fabric. In a case where a fiber material (a pulp) is used, the absorbing material is sandwiched between the fiber materials or blended with the fiber materials. Such fiber substrates are a crushed wood pulp, a cotton linter, a cross-linked cellulose fiber, hydrophilic fibers such as rayon, cotton, wool, acetate, vinylon, and the like. These fiber substrates are preferably air-laid.

In order to obtain the effect of the present invention, the content (a core concentration) of the particle-shaped water absorbing agent in the absorbing material for absorbing goods is in a range of 30 to 100% by weight, preferably in a range of 40 to 100% by weight, more preferably in a range of 50 to 100% by weight, further preferably in a range of 60 to 100% by weight, especially preferably in a range of 70 to 100% by weight, or most preferably in a range of 75 to 95% by weight.

For example, in a case where the particle-shaped water absorbing agent of the present invention of one of the concentrations above is used especially for an upper layer of the absorbing material, it is possible to improve an absorption amount of the whole absorbing good such as a paper diaper through an effective liquid distribution and provide the absorbing good whose absorbing material keeps a clean white color thereof because the particle-shaped water absorbing agent is excellent in diffusibility of absorbed liquid such as urine due to a high liquid permeability (liquid permeability under pressure).

The absorbing material is preferably performed compression formation in order that the concentration thereof may be in a range of 0.06 g/cc to 0.50 g/cc and the basis weight thereof may be in a range of 0.01 $g/cm^2$ to 0.20 $g/cm^2$. In addition, the thickness of the absorbing material is less than 30 mm or preferably less than 20 mm in order to provide an absorbing material which is suitable for thin paper diapers.

The present invention provides the followings:

(A) a particle-shaped water absorbing agent whose main component is a polyacrylic acid and/or a salt thereof, the particle-shaped water absorbing agent having a surface color of Hunter b value in a range of −5 to 10, more preferably −5 to 5, and further more preferably −3 to 3, and having a cross-linking absorption property index (CPI) in a range of 1 to 100, the CPI defined by the following equations:

$$GEX=(y+17)/\text{Ln}(x); \quad \text{Equation 1;}$$

$$CPI=(GEX/z)\times 100 \quad \text{Equation 3;}$$

(x is water soluble content (% by weight), y is absorbency under no load (GVs) (g/g), and z is residual monomer content (ppm by weight))

(B) a method for producing a particle-shaped water absorbing agent, the method including the steps of polymerizing an unsaturated-monomer aqueous solution containing an acrylic acid and/or a salt thereof as its main component, so as to obtaining a hydrous gel polymer, and drying the hydrous gel polymer, wherein the unsaturated-monomer aqueous solution contains a specific amount of an N-oxyl compound;

(C) a method for producing a particle-shaped water absorbing agent, the method including the steps of polymerizing an unsaturated-monomer aqueous solution containing an acrylic acid and/or a salt thereof as its main component, so as to obtaining a hydrous gel polymer, and drying the hydrous gel polymer, wherein the unsaturated-monomer aqueous solution contains a specific amount of a methoxyphenol and a manganese compound;

(D) a particle-shaped water absorbing agent whose main component is a polyacrylic acid and/or a salt thereof, the particle-shaped water absorbing agent including at least N-oxyl compound, wherein a surface color has a Hunter L value in a range of 90 to 100, a Hunter a value in a range of −1 to 1, and a Hunter b value in a range of −3 to 3;

(E) a particle-shaped water absorbing agent whose main component is a polyacrylic acid and/or a salt thereof, the particle-shaped water absorbing agent including at least a manganese compound, wherein a surface color has the Hunter L value in a range of 90 to 100, the Hunter a value in a range of −1 to 1, and the Hunter b value in a range of −3 to 3;

(F) a usage of the N-oxyl compound and the manganese compound as a color protection agent for the particle-shaped water absorbing agent containing the polyacrylic acid and/or the salt thereof as its main component;

(G) a particle-shaped water absorbing agent including: as its main component, a polyacrylic acid and/or a salt thereof; a polyalkyleneglycol; and an iron by iron content in a range of 0.001 to 10 ppm by weight;

(H) a method for producing a particle-shaped water absorbing agent, including adding or preparing a polyalkyleneglycol of weight average molecular weight of 300 to 50000 and iron in a range of 0.01 to 10% by weight and in a range of 0.001 to 10 ppm by weight respectively in an unsaturated-monomer aqueous solution which contains the acrylic acid and/or the salt thereof as its main component and which is not polymerized or is polymerized incompletely;

(I) a particle-shaped water absorbing agent including: an absorbing resin of a polyacrylic aid and/or a salt thereof; and a water-soluble thiodialkyl compound; and (J) a method for producing a particle-shaped water absorbing agent, including adding a water-soluble thiodialkyl compound in an unsaturated-monomer aqueous solution.

The present invention can provide (i) a particle-shaped water absorbing agent whose production is easily controllable, especially whose polymerization reaction is easily controllable, and is remarkably improved in surface color, and (ii) a method for manufacturing the particle-shaped water absorbing agent, which method is easily controllable especially in terms of the polymerization reaction. The particle-shaped water absorbing agent of the present invention includes at least one of a chelating agent, an α-hydroxylic acid and/or a salt thereof, and a reducing agent, so that the particle-shaped water absorbing agent can have remarkably improved long-term color stability without sacrificing physical properties. Further, the particle-shaped water absorbing agent of the present invention is therefore suitable especially for an absorber having high water absorbing resin content, and hygienic goods such as paper diapers and keeps a significantly white color with clean sensation even if stored under high temperature and high humidity for a long time.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

EXAMPLE

The present invention is described referring to Examples below. The present invention should not be construed such that it is limited to these examples. Moreover, various numerical values recited in the claims and Examples of the present invention were obtained by the following measuring methods. The measuring methods are explained based on particle-shaped water absorbing agent. For water-absorbing resin, the explanation of the measuring methods should be read by replacing the "particle-shaped water absorbing agent" with "water-absorbing resin". Moreover, the terms "mass" and "weight" are used synonymously in the present application. Thus, the wordings "ppm by weight" and "ppm by mass" (or simply "ppm") are exchangeable with each other, and the wordings "% by weight" and "% by mass" are exchangeable with each other.

(a) Particle Size

Following the method described in WO2004/069404, water-absorbing resin (or particle-shaped water absorbing agent) was classified with JIS standard sieves (JIS Z8801-1 (2000)) or a sieve equivalent thereto of the following mesh sizes: 850 μm, 710 μm, 600 μm, 500 μm, 425 μm, 300 μm, 212 μm, 150 μm, 106 μm, and 45 μm. Residual percentages R thus obtained were plotted to a logarithmic probability paper. From the plot, a particle size corresponding to R=50% by weight was read as a mass medium particle size (D50). Logarithmic standard deviation (δξ), which is expressed by the following Equation 5, indicates particle size distribution. The smaller δξ, the particle size distribution is narrower.

$$\delta\xi = 0.5 \times \ln(X2/X1)$$ Equation 5:

(where X1 was the particle diameter when R=84.1%, and X2 was the particle diameter when R=15.9%).

(b) Absorbency Against Pressure (AAP)

Referring to International Patent Publication WO 2006/109844 and International Patent Application WO 2007/JP/56527, absorbency against pressure (under load) for 0.9% by weight saline was measured.

An apparatus shown in FIG. 1 was used for the test. A stainless metal net 101 with 400 mesh size (pore size 38 μm) was fused at a bottom of a plastic supporting cylinder 100 made of with inner diameter of 60 mm. On the net 101, the water absorbing agent 102 (0.900 g) was evenly spread. A piston 103 and a load 104 were mounted in this order on the water absorbing agent 102. The piston 103 and a load 104 were provided such that (i) they were adjusted to be able to apply pressure of 1.9 kPa (0.3 psi) or 4.8 kPa (0.7 psi) evenly to the water absorbing agent 102, (ii) those external diameters were slightly less than 60 mm so that there was no gap between those and the supporter cylinder, and (iii) it was possible to smoothly move up and down. Weight W3 (g) of this measuring apparatus was measured.

A glass filter 106 (produced by SOGO RIKAGAKUGA-RASU SEISAKUSHO, pore diameter: 100 μm to 120 μm) whose diameter was 90 mm was placed inside a petri dish 105 whose diameter was 150 mm, and a 0.90 wt % saline 108 (20° C. to 25° C.) was poured to the petri dish 105 until the 0.90 wt % saline 108 reaches the same level in height as an upper surface of the glass filter. On the glass filter, a piece of filter paper 107 was placed so that the entire surface of the filter paper 107 got wet. The filter paper used here had a diameter of 90 mm (Product Name: (JIS P 3801, No. 2), produced by Advantec Toyo Kaisha, Ltd. 0.26 mm in thickness and capable of retaining particles of 5 μm in diameter). Then, the excess saline was removed.

The above measuring apparatus was mounted on the above wet filter paper, and the liquid was absorbed under load. One hour later, the measuring apparatus was removed, and its weight W4 (g) was measured. Then, the absorbency (g/g) for the 0.90 wt % saline against pressure was calculated by a following equation using W3 and W4.

$$AAP=(W4-W3)/0.90 \qquad \text{Equation 6:}$$

(c) Absorbency Under No Load ((Centrifuge Retention Capacity (CRC)/Absorbency Under No Load (GVs))

Into a nonwoven porch (60×60 mm, Heatron Paper made by Nangoku Pulp Kogyo Co., Ltd., model type: GSP-22), 0.2 g of particle-shaped water absorbing agent was placed and heat-sealed. Then, the porch was immersed in 100 g of 0.9 wt % saline at 25 (+/−3)° C. After 60 min from the immersing, the porch was removed out of the saline and centrifuged with a centrifuging apparatus at 250 G for 3 min. Then, the nonwoven porch was measured to find weight W1. This procedure was carried out again without the particle-shaped water absorbing agent to find weight W2. From Equation 7, the absorbency was calculated out.

$$GVs=(W1-W2)/0.2-1 \qquad \text{Equation 7:}$$

(d) Water Soluble Polymer Content (May be Abbreviated as Soluble Amount or Soluble Content)

Into a lidded plastic container of 250 ml, 184.3 g of 0.90 wt % saline was measured. After adding 1.00 g of the particle-shaped water absorbing agent therein, the aqueous solution was stirred from 16 hours to extract the soluble content in the resin. The extract was filtered via a piece of filter paper ((Product Name: (JIS P 3801, No. 2), produced by Advantec Toyo Kaisha, Ltd. 0.26 mm in thickness and capable of retaining particles of 5 μm in diameter), thereby obtaining a filtrate, 50 g of which was then weighted to obtain a measuring solution.

First, the saline was titrated by using NaOH aqueous solution of 0.1N until pH10 was obtained. After that, the 0.90 wt % saline was titrated by using HCl aqueous solution of 0.1N until pH2.7 was obtained. In this way, controls ([bNaOH] ml, [bHCl] ml) were obtained. The measurement solution was titrated in the same way as above in order to obtain titer ([NaOH] ml, [HCl] ml). For example, in case of the particle-shaped water absorbing agent formed from an acrylic acid and its salt in a known amount, soluble content (mainly extracted water-soluble polymer) of the particle-shaped water absorbing agent can be calculated from the following Equation 8 based on the average molecular weight of its monomer and the titer thus obtained in the above-explained procedure. In case the amount of acrylic acid and its salt in the particle-shaped absorbing agent is unknown, the molecular weight of the monomer is calculated out from neutralization ratio worked out from the titer based on the following Equation 9.

$$\text{Soluble Content (wt \%)=0.1×(Average Molecular Weight)×184.3×100([HCl]-[bHCl])/1000/1.0/50.0} \qquad \text{Equation 8:}$$

$$\text{Neutralization Ratio (mol \%) (1-([NaOH]-[bNaOH]/([HCl]-[bHCl])×100} \qquad \text{Equation 9:}$$

(e) Coloring Evaluation of Particle-Shaped Water Absorbing Agent (Surface Color Evaluation)

Coloring evaluation of the particle-shaped water absorbing agent was carried out by using spectrometric colorimeter SZ-Σ80 Color Measuring System (made by Nippon Denshoku Industries Co., Ltd.). The measuring was carried out by reflection analysis, using a container for powder/paste sample. The container, which was an accessory of this spectrometric colorimeter, had an internal diameter of 30 mm and height of 12 mm. As a control, standard round white board No. 2 for power and paste was used. Further, 30 Φ lighting pipe was used. In the above-explained container accessory to the spectrometric colorimeter, the water-absorbing polymer of about 5 g was placed to fill the container by about 60%. At room temperature (in a range of 20 to 25° C.) and under humidity of 30 to 50RH %, L value (lightness: psychometric lightness) of the surface of the water-absorbing polymer was measured with the use of spectrometric colorimeter.

Moreover, using the same apparatus and measuring method, other color parameters values a, b (chromaticity) or YI (yellow index) or WB (white balance) can be measured. The greater WB and smaller YI/a/b, the lower the coloring and closer to white.

Moreover, evaluation of the long-term color stability was carried out by the evaluation method and conditions described in the international patent application WO 2007/JP/67348 (filed on Aug. 30, 2007).

(f) Residual Monomer

Using the filtrate separately prepared in (d) and stirred for 2 hours, the residual monomer content (residual acrylic acid and/or salt thereof content) in the particle-shaped water absorbing agent was measured in ppm (based to the particle-shaped water absorbing agent) by UV analysis via a liquid chromatography. Moreover, the residual monomer content in the hydrous gel before drying was worked out by UV analysis performed in a similar manner by via the liquid chromatography using fragmented hydrous gel containing about 500 mg of resin solid content and being stirred for 16 hours, and then correcting the result of the UV analysis by subtracting the solid content therefrom.

(g) GEX Value and CPI Value

Following the method described in US Patent Application Publication No. 20060167198, GEX value was calculated out from the above-identified definitional equation. Moreover, from the GEX value and the residual monomer amount, the CPI value was calculated out from the definitional described above.

(h) Solid Content

In an aluminum cup of about 50 mm in diameter at bottom, 1.00 g of the particle-shaped water absorbing agent was weighed. Then, total weight W8 (g) of the absorbing resin and aluminum cup was measured. After that, the particle-shaped water absorbing agent in the aluminum cup was placed in an oven to be place in an environment of a temperature of 180° C. for 3 hours. After 3 hours, the absorbing resin and aluminum cup were taken out of the oven and cooled in a desiccator to room temperature sufficiently. Total weight W9 (g) of the dried water absorbing agent and aluminum cup was measured. The solid content was calculated out from Equation 10.

$$\text{Solid Content (wt \%)=100-((W8-W9)/(Weight of Water Absorbing agent Resin (g))×100} \qquad \text{Equation 10}$$

(i) Iron (Fe) Content in Particle-Shaped Water Absorbing Resin

In a platinum crucible, 1.000 g of particle-shaped water absorbing agent was measured. Then, the particle-shaped water absorbing agent was heated in an electric furnace (made of Yamato Scientific Co. Ltd.: Muffle Furnace FO300) so as to ash the particle-shaped water absorbing agent.

Into the platinum crucible removed from the electric furnace, about 5 ml of nitric acid aqueous solution (an 1:1 aqueous solution of special-grade nitric acid (Wako Pure Chemicals Industries Ltd.) and ion exchanged water) so as to dissolve the ash, and then ion exchanged water was further added therein. Thereby, about 15 ml of an aqueous solution of the ash was obtained.

Platinum crucible without the particle-shaped water absorbing agent therein was treated in the same way to be a blank.

The aqueous solution thus prepared in the above way was analyzed in Fe content by ICP emission spectro-photometric analysis as described in JISK 1200-6. The ICP emission spectro-photometric analyzer was ULTIMA made by Horiba Ltd.

The manganese content and copper content were analyzed in the similar manner in the present invention.

Production Example 1

A commercially-available acrylic acid (Wako Pure Chemicals Industries Ltd.; Special Grade, containing p-methoxyphenol by 200 ppm by weight), which was produced by gas phase catalytic oxidation, was supplied to a bottom of separating tower for high-boiling point impurity and distilled at reflux rate of 1. The separating tower had 50 non-stopping porous plates. The distillation was repeated once more. In this ways, a pure acrylic acid (1) having acrylic acid by 99% or more with a small amount of impurity (mainly water) was obtained. In the pure acrylic acid (1), p-methoxyphenol content was ND (less than 1 ppm by weight), protoanemonin content, furfural content, β-hydroxypropione acid content, acrylic acid dimmer content were ND (less than 1 ppm by weight). Moreover, in the pure acrylic acid (1), phenothazien content was 0 ppm by weight, aldehyde content and maleic acid content were 1 ppm by weight or less, and acetic acid content and propionic acid content were 200 ppm by weight.

The pure acrylic acid (1) was mixed with p-methoxyphenol by 3.5 ppm by weight and manganese acetate by 0.5 ppm by weight, thereby obtaining a modified acrylic acid (1).

Production Example 2

A modified acrylic acid (2) was prepared in the same manner as in Production Example 1 except that the pure acrylic acid (1) was mixed with 2,2,6,6-tetraperilidine-1-oxyl by 1 ppm by weight.

Production Example 3

A modified acrylic acid (3) was prepared in the same manner as in Production Example 1 except that the pure acrylic acid (1) was mixed with p-methoxyphenol by 100 ppm by weight.

Production Example 4

Into a 5 L 5-necked flask with two dropping funnel, a pH meter, a thermometer, and stirring blades, 1598 g of ion exchanged water was poured. Moreover, 1280 g of the modified acrylic acid (1), which was substantially acrylic acid at room temperature, was introduced in one of the dropping funnel, while 1488 g of an aqueous solution of 48 wt % sodium hydroxide (Fe 0.5 ppm by weight (as $Fe_2O_3$ and Copper N.D. as CuO) aqueous solution at room temperature was in the other dropping funnel. The 5 L flask was immersed in a water bath. Next, while stirring a neutralization reaction system inside the 5 L flask kept at 35° C. or less, the 48 wt % sodium hydroxide aqueous solution and modified acrylic acid (1) were dropped in the flask at the same time. The dropping of the modified acrylic acid (1) was finished in about 35 min, and the dropping of the 48 wt % sodium hydroxide aqueous solution was finished in about 45 min. After the ends of the dropping of the modified acrylic acid (1), the dropping funnel was washed with 100 g of ion exchanged water, which was then flowed into the flask. After the ends of the dropping of the 48 wt % sodium hydroxide aqueous solution, the dropping funnel was washed with 100 g of ion exchanged water, which was then flowed into the flask. After all the dropping was completed, the solution was adjusted to a temperature in a range of 20 to 35° C., and 20-minutes curing was carried out. After the curing, a very small amount of the modified acrylic acid (1) was dropped therein to adjust pH to 10 (+/−0.1). In this ways, a sodium acrylate aqueous solution (1) was prepared, whose concentration was 37% by weight and neutralization ration was 100 mol %.

Production Examples 5 and 6

In the same manner except the modified acrylic acid (1) in Production Example 4 with the modified acrylic acid (2) or (3), sodium acrylate aqueous solutions (2) and (3) were prepared, whose concentration was 37% by weight and neutralization ration was 100 mol %.

Example 1

As a polymerization apparatus, a kneader was used, which had two stainless arms and a vessel of 10 L in internal volume and coated with Teflon (registered trademark) inside, and jacketed. The kneader had two sigma type blades of 120 mm in rotation diameter and a lid for sealing the system. Three hundred and seventy six point three gram (376.3 g) of the modified acrylic acid (1), and 3983 g of sodium acrylate (1), which was neutralized product of the modified acrylic acid (1), 640.7 g of ion exchanged water, and 0.10 mol % (to the total number of moles of the monomer) of polyethyleneglycoldiacrylate (internal cross-linking agent: ethyleneoxide average addition mole number=8.2) were mixed to prepare a monomer aqueous solution (1) whose concentration was 37% by weight and neutralization ratio was 75 mol %.

Further, the monomer aqueous solution (1) kept at 22° C. was poured in the sigma-type two-armed kneader and exposed to nitrogen gas flowing therein, whereby the oxygen in the system was replaced with nitrogen to dissolved oxygen content of 1 ppm or less. Then, with the monomer solution (1) stirred and warm water passing the jacket through, the polymerization was initiated by adding an aqueous solution of sodium persulfate (0.09 g/mol) and L-ascorbic acid (0.005 g/mol) therein. The polymerization was initiated in a predetermined time, and carried on while fragmenting polymer gel being produced. The polymerization was continued for 20 min after a peak temperature was reached. Thereby, a cross-linked polymer (1) in a hydrous gel form fragmented into diameters of about 1 to 2 mm. Immediately after the polymerization, the resultant polymer (1) was spread over a 850 μm metal net and dried with hot air for 90 min at 180° C. with a dew point of 70° C. Next, the dried was crushed with a vibration mill and classified with a JIS 850 μm standard sieve, thereby obtaining a particle-shaped water absorbing agent (1), which passed through the sieve.

Example 2

A particle shaped water absorbing agent (2) was prepared in the same way as in Example 1 except that the modified acrylic acid (2) and the sodium acrylate aqueous solution (2) were used instead.

Example 3

To 100 parts by weight of the particle-shaped water absorbing agent (1), a surface cross-linking agent was sprayed and mixed, which contained 0.4 parts by weight of 1,4-butanediol, 0.6 parts by weight of propyreneglycol, 3.0 parts by weight of ion exchange water, and 0.5 parts by weight of isopropanol (based on weight of the passed through the sieve). Further, the particle-shaped water absorbing agent (1) was heated at 210° C. for 40 min. Thereby, surface-crosslinked particle-shaped water absorbing agent (3) was prepared, whose properties were as follows: GVs=34 g/g, AAP1.9 kPa=28 g/g, AAP4.8 kPa=25 g/g, SFC=10 $(cm^3 \cdot s \cdot 10^{-7}/g)$.

Example 4

Into a propylene container of 80 mm in internal diameter and 1 L in volume, which was wrapped with expanded polystyrene acting as a thermal insulator, a solution (A) was prepared, which contained 184.01 g of the modified acrylic acid (1) and 1.29 g of polyethyleneglycoldiacrylate (molecular weight 523). Then, the solution (A) was mixed with a solution (B), which contained 153.74 g of 48.5 wt % sodium hydroxide aqueous solution (Fe 0.5 ppm by weight (as $Fe_2O_3$) and copper N.D. (as CuO)), and 145.15 g of ion exchanged water adjusted to 50° C. The mixing of the solutions (A) and (B) was carried out in such a manner that the solution (B) was quickly added in the solution (A) stirred with a magnetic stirrer. In this way, a monomer aqueous solution (C) was prepared. Due to neutralization heat and dissolving heat, temperature of the monomer aqueous solution (C) was increased to about 100° C.

Next, into the monomer aqueous solution (C), 10.2 g of 3 wt % sodium persulfate aqueous solution was added with stirring. Immediately after that, the monomer aqueous solution was poured in a stainless vat sized 250×250 mm at bottom and internally coated with Teflon (registered trademark) without a lid thereon, the container being heated to 100° C. by using a hot plate (NEO HOT PLATE H1-1000 (Inouchi Seieido Co., Ltd.). The stainless vat had a size of 250×250 mm at bottom, 640×640 mm on top surface, and 50 mm in height, and a trapezoidal cross-sectional shape and is opened on the top.

Soon after the monomer aqueous solution (C) was poured in the vat, the polymerization was started. The polymerization was carried on with vapor and swelling foaming in all direction and then shrinking to a size slightly larger than the bottom surface. The swelling and shrinking took place in about 1 min. After kept in the polymer vessel for 4 min, the hydrous polymer (hydrous gel) was taken out therefrom. These procedures were carried out atmospheric environment.

The resultant hydrous polymer (hydrous gel) was crushed by a meat chopper, thereby obtaining a hydrous polymer (fragmented gel particles) of several mm in size.

The fragmented gel particles was spread over a 20-mesh (mesh size: 850 μm) metal net and dried at 180° C. for 30 min with hot air. The dried was crushed with a roll mill, and then classified with JIS standard sieves of 850 μm and 150 μm mesh sizes. In this way, a particle-shaped water absorbing agent (4) (solid content 96 wt %) was obtained.

Comparative Example 1

A comparative particle-shaped water absorbing agent was obtained in the same manner except that the modified acrylic acid (3) and the sodium acrylate aqueous solution (3) were used instead.

Results of the particle-shaped water absorbing agents (1) to (4) and the comparative particle-shaped water absorbing agent (1) are shown in Table 1.

Example 5

To be evaluate properties as an absorbing agent, an absorbing agent was prepared and rewetting amount and outer appearance of the absorbing agent were evaluated. How to prepare the absorbing agent for evaluation was explained below.

Four parts by weight of the particle-shaped water absorbing agent and 1 parts by weight of wood-crushed pulp were dry-mixed with a mixer. Next, the resultant mixture was spread over a wire screen with 400 mesh (mesh size 38 μm), and formed into a web of diameter of 90 mm φ. Further, the web was pressed for 1 min with a pressure of 196.14 kPa (2 kgf/cm²), thereby obtaining an absorbing agent for evaluation. The absorbing agent evaluation had a basic weight of about 0.05 g/cm². How to evaluate 10 min rewetting amount is shown below.

At a bottom of a Petri dish made by SUS and having an internal diameter of 90 mm φ, the absorbing agent for evaluation was placed and a nonwoven cloth of 90 mm φ was placed on the top of it. Then, 30 ml of saline (0.9% sodium chloride aqueous solution) was poured on the nonwoven cloth and absorbed under no load for 10 min. Then, 30 pieces of filter paper (No. 2; produced by Toyo Roshi Kaisha, Ltd.) whose outer diameter was 90 mm φ and whose total weight (W7 (g)) was measured in advance was placed on the absorbing agent. Then, a piston and weight, which could place a load on the absorbing agent, nonwoven cloth, and filter paper evenly (total weight of the piston and weight was 20 kg) was placed on the filter paper. In this way, load was placed thereon for 5 min thereby letting the filter paper to absorb the return of the absorbed liquid. Then, the 30 pieces of filter paper was weighted (W8 (g)). From the following equation, 10 min rewetting amount was measured, which was 3 g.

10 min rewetting amount (g)=*W*8 (g)−*W*7 (g)  Equation 2:

Moreover, the outer appearance was evaluated visually to find that the adsorbent was white and gave a sensation of cleanness.

Comparative Example 2

An absorbing agent was evaluated in the same manner as in Example 5 except that the comparative particle-shaped water absorbing agent was used instead. The evaluation showed that a rewetting amount was 6 g and the comparative particle-shaped water absorbing agent (1) had yellowish outer appearance.

TABLE 1

|  |  | D50 (μm) | GVs (g/g) | Soluble Content (%) | Residual Monomer Content (ppm by weight) | Hunter Lab on Surface Color System | | | | |
|---|---|---|---|---|---|---|---|---|---|---|
|  |  |  |  |  |  | L | a | b | GEX | CPI |
| Ex. 1 | Absorbing Agent (1) | 440 | 42 | 10.1 | 500 | 91 | −0.2 | 1.3 | 25.5 | 5.1 |
| Ex. 2 | Absorbing Agent (2) | 450 | 41 | 10.7 | 500 | 92 | 0 | 1.3 | 24.5 | 4.9 |
| Ex. 3 | Absorbing Agent (3) | 380 | 34 | 12 | 500 | 90.7 | −0.1 | 1.4 | 20.5 | 4.1 |
| Ex. 4 | Absorbing Agent (4) | 500 | 43 | 10.1 | 500 | 93 | 0 | 1 | 25.9 | 5.2 |
| Com. Ex. 1 | Comparative Absorbing Agent (1) | 400 | 40 | 10.9 | 500 | 87 | −0.3 | 4 | 23.9 | 4.8 |

Abbreviation:
Ex. stands for Example.
Com. Ex. stands for Comparative Example.
Absorbing Agent stands for Particle-Shaped Water Absorbing Agent.
Comparative Absorbing Agent stands for Comparative Particle-Shaped Water Absorbing Agent.

Production Example 7

Preparation Method of 37 Wt % Sodium Acrylate Aqueous Solution (SA1)

Into a 5 L 4-necked flask with two dropping funnel, a pH meter, a thermometer, and stirring blades, 1598 g of ion exchanged water was poured. Moreover, 1280 g of an acrylic acid at room temperature was introduced in one of the dropping funnel, while 1488 g of an aqueous solution of 48.5 wt % sodium hydroxide aqueous solution (Kaname Chemicals Co., Ltd.) at room temperature was in the other dropping funnel. The 5 L flask was immersed in a water bath. The 48.5 wt % sodium hydroxide aqueous solution was analyzed in Fe content by the ICP emission spectro-photometric analysis as described in JISK 1200-6. The Fe content thereof was 0.35 ppm by weight.

Next, while stirring a neutralization reaction system inside the 5 L flask kept at 45° C. or less, the 48.5 wt % sodium hydroxide aqueous solution and modified acrylic acid (1) were dropped in the flask at the same time. The dropping of the acrylic acid was finished in about 35 min, and the dropping of the 48.5 wt % sodium hydroxide aqueous solution was finished in about 45 min. After the ends of the dropping of the acrylic acid, the dropping funnel was washed with 100 g of ion exchanged water, which was then flowed into the flask. After the ends of the dropping of the 48.5 wt % sodium hydroxide aqueous solution, the dropping funnel was washed with 100 g of ion exchanged water, which was then flowed into the flask. After all the dropping was completed, the solution was adjusted to a temperature in a range of 20 to 35° C., and 20-minutes curing was carried out. After the curing, a very small amount of the acrylic acid was dropped therein to adjust pH to 10 (+/−0.1). In this ways, a sodium acrylate aqueous solution (SA1) was prepared, whose concentration was 37% by weight and neutralization ration was 100 mol %.

Production Example 8

Preparation Method of 37 Wt % Sodium Acrylate Aqueous Solution (SA2)

A sodium acrylate aqueous solution (SA2), whose concentration was 37 wt % and neutralization of 100 mol %, was prepared in the same manner as in Production Example 7 except that a mixture of the 48.5 wt % sodium hydroxide aqueous solution and ferrous sulfate ($FeSO_4 \cdot 7H_2O$, Wako Pure Chemicals Industries Ltd.) was used instead, which had Fe content of 1.58 ppm by weight according to the ICP emission spectro-photometric analysis as described in JISK 1200-6.

Production Example 9

Preparation Method of 37 Wt % Sodium Acrylate Aqueous Solution (SA3)

A sodium acrylate aqueous solution (SA3), whose concentration was 37 wt % and neutralization of 100 mol %, was prepared in the same manner as in Production Example 7 except that a mixture of the 48.5 wt % sodium hydroxide aqueous solution and ferrous sulfate ($FeSO_4 \cdot 7H_2O$, Wako Pure Chemicals Industries Ltd.) was used instead, which had Fe content of 10.01 ppm by weight according to the ICP emission spectro-photometric analysis as described in JISK 1200-6.

Production Example 10

Preparation Method of 37 Wt % Sodium Acrylate Aqueous Solution (SA4)

A sodium acrylate aqueous solution (SA4), whose concentration was 37 wt % and neutralization of 100 mol %, was prepared in the same manner as in Production Example 7 except that the 48.5 wt % sodium hydroxide aqueous solution was replaced with CLEARCUT-S 48% made by Tsurumi Soda Co., Ltd. The CLEARCUT-S 48% had Fe content of 5 ppb by weight according to ICP emission spectro-photometric analysis.

Example 6

In a reaction vessel prepared by providing a lid to the stainless two-armed kneader with two sigma type blades, 10 L internal volume and a jacket, 470.6 g of acrylic acid, 4376.7 g of 37 wt % sodium acrylate (SA1) obtained in Production Example 7, 576.6 g of pure water, 12.4 g of polyethyleneglycoldiacrylate (molecular weight 523), and 20.9 g of polyethyleneglycol 20,000 (average molecular weight 20,000, Wako Pure Chemical Industries Co., Ltd.) were dissolved to prepare a reaction solution. In the reaction solution, p-methoxyphenol content was approximately 50 ppm by weight, and protoanemonin content, furfural content, β-hydroxypropione acid content, acrylic acid dimmer content were ND (less than 1 ppm by weight). Moreover, phenothazien content was 0 ppm by weight, aldehyde content and maleic acid content were 1 ppm by weight or less, and acetic acid content and propionic acid content were 200 ppm by weight.

Next, the reaction solution was deaerated for 20 min under nitrogen gas atmosphere at a temperature adjusted to 25° C. Then, 19.0 g of 15 wt % sodium persulfate aqueous solution and 23.7 g of 0.1 wt % L-ascorbic acid aqueous solution was added therein with stirring. This initiated polymerization 30 second later at a polymerization initiation temperature of 25.2° C.

The polymerization was carried on at temperatures in a range of 25 to 95° C., while crushing produced gel. Thirty min after the start of the polymerization, a hydrogenous gel crosslinked polymer was taken out of the reaction vessel. The resultant hydrous gel crosslinked polymer has fragmented diameters of about 10 mm or less.

The fragmented hydrous gel crosslinked polymer was spread over a stainless metal net of mesh size of 850 μm and dried at 180° C. for 45 min with hot air. The dried was crushed with a roll mill (WML type roll crusher, made by Inoguchi Giken Co., Ltd.), and then classified with JIS standard sieves of mesh sizes of 600 μm and 300 μm. Thereby, a particle-shaped water absorbing agent (5) (solid content 95 wt %) was obtained, whose properties are shown in Tables 2 and 3.

Example 7

A particle-shaped water absorbing agent (6) (solid content 95 wt %) was prepared in the sample way as in Example 6, except that the 37 wt % sodium acrylate aqueous solution (SA2) obtained in Production Example 8 was used instead. Properties of the particle-shaped water absorbing agent (6) are shown in Tables 2 and 3.

Example 8

Into a propylene container of 80 mm in internal diameter and 1 L in volume, 368.68 g of acrylic acid, a solution (A) was prepared which contained 1.48 g of polyethyleneglycoldiacrylate (molecular weight 523), and 2.25 g of 1.0 wt % diethylenetriamin5 acetate.3 sodium aqueous solution. Then, the solution (A) was mixed with a solution (B), which contained 288.27 g of 48.5 wt % sodium hydroxide aqueous solution, and 321.04 g of ion exchanged water adjusted to 50° C. The mixing of the solutions (A) and (B) was carried out in such a manner that the solution (B) was quickly added in the solution (A) stirred with a magnetic stirrer. In this way, a monomer aqueous solution (C) was prepared. The 48.5 wt % sodium hydroxide aqueous solution was made by Kaname Chemicals Co., Ltd. as in Production Example 7. In the monomer aqueous solution (C), p-methoxyphenol content was approximately 50 ppm by weight, and protoanemonin content, furfural content, β-hydroxypropione acid content, acrylic acid dimmer content were ND (less than 1 ppm by weight). Moreover, phenothazien content was 0 ppm by weight, aldehyde content and maleic acid content were 1 ppm by weight or less, and acetic acid content and propionic acid content were 200 ppm by weight.

Due to neutralization heat and dissolving heat, temperature of the monomer aqueous solution (C) was increased to 102° C. The monomer aqueous solution (C) was mixed with 9.00 g of polyethyleneglycol 600 (average molecular weight 600, Wako Pure Chemicals Industries Ltd.) with stirring, thereby obtaining a monomer aqueous solution (D).

After the temperature of the monomer aqueous solution (D) was cooled to 97° C., 13.81 g of 3 wt % sodium persulfate aqueous solution was added therein with stirring. Immediately after that, the monomer aqueous solution was poured in a stainless vat sized 250×250 mm at bottom and internally coated with Teflon (registered trademark) without a lid thereon, the container being heated to 100° C. by using a hot plate (NEO HOT PLATE H1-1000 (Inouchi Seieido Co., Ltd.). The stainless vat had a size of 250×250 mm at bottom, 640×640 mm on top surface, and 50 mm in height, and a trapezoidal cross-sectional shape and is opened on the top.

Soon after the monomer aqueous solution (D) was poured in the vat, the polymerization was started. The polymerization was carried on with vapor and swelling foaming in all direction and then shrinking to a size slightly larger than the bottom surface. The swelling and shrinking took place in about 1 min. After kept in the polymer vessel for 3 min, the hydrous polymer (hydrous gel) was taken out therefrom. These procedures were carried out atmospheric environment.

The resultant hydrous polymer (hydrous gel) was crushed by a meat chopper, thereby obtaining a hydrous polymer (fragmented gel particles) of several mm in size.

The fragmented gel particles was spread over a stainless metal net (mesh size: 850 μm) and dried at 180° C. for 30 min with hot air. The dried was crushed with a roll mill (WML-type roll crusher made by Inoguchi Giken Co., Ltd.), and then classified with JIS standard sieves of 600 μm and 300 μm mesh sizes. In this way, a particle-shaped water absorbing agent (7) (solid content 96 wt %) was obtained. Properties of the particle-shaped water absorbing agent (7) are shown in Tables 2 and 3.

Example 9

A particle-shaped water absorbing agent (8) (solid content 95 wt %) was obtained in the same way as in Example 8 except that polyethyleneglycol 2,000 (average molecular weight 2,000, Wako Pure Chemicals Industries Ltd.) was added as the polyethyleneglycol to be added in the monomer aqueous solution (C). Properties of the particle-shaped water absorbing agent (8) are shown in Tables 2 and 3.

Example 10

A particle-shaped water absorbing agent (9) (solid content 96 wt %) was obtained in the same way as in Example 8 except that polyethyleneglycol 6,000 (average molecular weight 6,000, Kanto Chemical Co., Ltd.) was added as the polyethyleneglycol to be added in the monomer aqueous solution (C). Properties of the particle-shaped water absorbing agent (9) are shown in Tables 2 and 3.

Example 11

A particle-shaped water absorbing agent (10) (solid content 96 wt %) was obtained in the same way as in Example 10 except that 0.45 g of polyethyleneglycol 6,000 (average molecular weight 6,000, Kanto Chemical Co., Ltd.) was added as the polyethyleneglycol to be added in the monomer aqueous solution (C). Properties of the particle-shaped water absorbing agent (10) are shown in Tables 2 and 3.

Example 12

A particle-shaped water absorbing agent (11) (solid content 96 wt %) was obtained in the same way as in Example 10 except that 2.25 g of polyethyleneglycol 6,000 (average molecular weight 6,000, Kanto Chemical Co., Ltd.) was added as the polyethyleneglycol to be added in the monomer aqueous solution (C). Properties of the particle-shaped water absorbing agent (11) are shown in Tables 2 and 3.

Example 13

A particle-shaped water absorbing agent (12) (solid content 96 wt %) was obtained in the same way as in Example 10 except that 18.00 g of polyethyleneglycol 6,000 (average molecular weight 6,000, Kanto Chemical Co., Ltd.) was added as the polyethyleneglycol to be added in the monomer aqueous solution (C). Properties of the particle-shaped water absorbing agent (12) are shown in Tables 2 and 3.

Example 14

A particle-shaped water absorbing agent (13) (solid content 95 wt %) was obtained in the same way as in Example 12 except that polyethyleneglycol 6,000 (average molecular weight 6,000) was replaced with polyoxyethylenealkylether (Nippon Shokubai Co., Ltd. Product Name (Softanol 500)). Properties of the particle-shaped water absorbing agent (13) are shown in Tables 2 and 3.

Example 15

A particle-shaped water absorbing agent (14) (solid content 95 wt %) was obtained in the same way as in Example 12 except that polyethyleneglycol 6,000 (average molecular weight 6,000) was replaced with methoxypolyethyleneglycol 2,000 (average molecular weight 2,000, Sigma Aldrich Japan). Properties of the particle-shaped water absorbing agent (14) are shown in Tables 2 and 3.

Example 16

To 100 parts by weight of the particle-shaped water absorbing agent (11) obtained in Example 12, a surface cross-linking agent solution was evenly mixed, which contains a mixture liquid of 0.3 parts by weight of 1,4-butanediol, 0.5 parts by weight of propyleneglycol, and 2.7 parts by weight of pure water. The water absorbing agent mixed with the surface cross-linking agent was heated for a predetermined time in a heating apparatus with stirring blades and jacket (jacket temperature: 210° C.). After the heat treatment, the resultant absorbing agent was passed through a JIS 600 μm standard sieve, thereby obtaining particle-shaped water absorbing agent (15) whose surface was crosslinked. Properties of the particle-shaped water absorbing agent (15) are shown in Tables 2 and 3.

Example 17

The particles prepared by crushing with the roll mill (WML type roll crusher, made by Inoguchi Giken Co., Ltd.) in Example 6 were classified with a JIS standard sieve thereby obtaining a particle-shaped water absorbing agent in which particles thereof were less than 850 μm in diameter and had D50 of 461 μm, 28 wt % of the particles were not less than 600 μm but less than 850 μm in diameter, 2.2 wt % of the particles were less than 150 μm in diameter, logarithmic standard deviation (σξ) of 0.364, solid content of 96 wt %. To 100 parts by weigh of the resultant water absorbing agent, a surface, a surface cross-linking agent solution was evenly mixed, which contains a mixture liquid of 0.3 parts by weight of 1,4-butanediol, 0.5 parts by weight of propyleneglycol, and 2.7 parts by weight of pure water, as in Example 16. The water absorbing agent mixed with the surface cross-linking agent was heated for a predetermined time in a heating apparatus with stirring blades and jacket (jacket temperature: 210° C.). After the heat treatment, the resultant absorbing agent was passed through a JIS 850 μm standard sieve, thereby obtaining particle-shaped water absorbing agent (16) whose surface was cross-linked. Properties of the particle-shaped water absorbing agent (16) are shown in Table 4.

Example 18

A particle-shaped water absorbing agent (17) was prepared in the same manner as in Example 17 except that the particles prepared by crushing with the roll mill (WML type roll crusher, made by Inoguchi Giken Co., Ltd.) in Example 7 were used instead. Properties of the particle-shaped water absorbing agent (17) are shown in Table 4.

Comparative Example 3

A comparative particle-shaped water absorbing agent (2) (solid content 96 wt %) was prepared in the same way as in Example 6 except that the polyethyleneglycol 20,000 (average molecular weight 20,000, Wako Pure Chemicals Industries Ltd.) was not used. Properties of the comparative particle-shaped water absorbing agent (2) are shown in Tables 2 and 3.

Comparative Example 4

A comparative particle-shaped water absorbing agent (3) (solid content 96 wt %) was prepared in the same way as in Comparative Example 3 except that the 37 wt % sodium acrylate aqueous solution (SA3) obtained in Production Example 9 was used instead. Properties of the comparative particle-shaped water absorbing agent (3) are shown in Tables 2 and 3.

Comparative Example 5

Polymerization was attempted in the same way as in Comparative Example 3 except that the 37 wt % sodium acrylate aqueous solution (SA4) obtained in Production Example 10 was used instead. The polymerization was not initiated even 30 min after the addition of the sodium persulfate aqueous solution and L-ascorbic acid aqueous solution. Thus, no particle-shaped water absorbing agent was obtained.

Comparative Example 6

A comparative particle-shaped water absorbing agent (4) (solid content 95 wt %) was prepared in the same way as in Example 8 except that polyethyleneglycol 600 (average molecular weight 600, Wako Chemical) was not used. Properties of the comparative particle-shaped water absorbing agent (4) are shown in Tables 2 and 3.

Comparative Example 7

A comparative particle-shaped water absorbing agent (5) (solid content 96 wt %) was prepared in the same way as in Example 12 except that polyethyleneglycol 6,000 (average molecular weight 6,000, Wako Chemical) to be added to the monomer aqueous solution (C) was replaced with diethyleneglycol (Wako Pure Chemicals Industries Ltd.). Properties of the comparative particle-shaped water absorbing agent (5) are shown in Tables 2 and 3.

Comparative Example 8

A surface cross-linked comparative particle-shaped water absorbing agent (6) was prepared in the same manner as in Example 17 except that the particles prepared by crushing with the roll mill (WML type roll crusher, made by Inoguchi Giken Co., Ltd.) in Comparative Example 3 were used instead. Properties of the comparative particle-shaped water absorbing agent (6) are shown in Tables 2 and 3.

Comparative Example 9

A surface cross-linked comparative particle-shaped water absorbing agent (7) was prepared in the same manner as in Example 17 except that the particles prepared by crushing with the roll mill (WML type roll crusher, made by Inoguchi Giken Co., Ltd.) in Comparative Example 4 were used instead. Properties of the comparative particle-shaped water absorbing agent (7) are shown in Tables 2 and 3.

TABLE 3

| | | Fe Content in Absorbing Agent (ppm by weight) |
|---|---|---|
| Ex. 6 | Absorbing Agent (5) | 0.66 |
| Ex. 7 | Absorbing Agent (6) | 2.97 |
| Ex. 8 | Absorbing Agent (7) | 0.62 |
| Ex. 9 | Absorbing Agent (8) | 0.67 |
| Ex. 10 | Absorbing Agent (9) | 0.69 |
| Ex. 11 | Absorbing Agent (10) | — |
| Ex. 12 | Absorbing Agent (11) | 0.72 |
| Ex. 13 | Absorbing Agent (12) | 0.74 |
| Ex. 14 | Absorbing Agent (13) | 0.83 |
| Ex. 15 | Absorbing Agent (14) | 0.64 |
| Com. Ex. 3 | Com. Absorbing Agent (2) | 0.64 |
| Com. Ex. 4 | Com. Absorbing Agent (3) | 9.17 |
| Com. Ex. 6 | Com. Absorbing Agent (4) | 0.62 |
| Com. Ex. 7 | Com. Absorbing Agent (5) | — |

Abbreviation:
Ex. stands for Example.
Com. Ex. stands for Comparative Example.
Absorbing Agent stands for Particle-Shaped Water Absorbing Agent.
Comparative Absorbing Agent stands for Comparative Particle-Shaped Water Absorbing Agent.

TABLE 2

| | | Type of Polyalkyleneglycol | Polyalkyleneglycol Content | Hunter Lab | | | YI | W (Lab) | WB | GVs (g/g) | Soluble Content (%) | RMC (ppm by weight) | GEX | CPI |
|---|---|---|---|---|---|---|---|---|---|---|---|---|---|---|
| | | | | L | a | b | | | | | | | | |
| Ex. 6 | Absorbing Agent (5) | PEG20,000 | 2% | 93.50 | −0.21 | 2.56 | 4.93 | 93.02 | 84.18 | 39.9 | 7.4 | 290 | 28.4 | 9.8 |
| Ex. 7 | Absorbing Agent (6) | PEG20,000 | 2% | 93.16 | −0.66 | 3.20 | 5.84 | 92.42 | 82.69 | 40.1 | 7.5 | 342 | 28.3 | 8.3 |
| Ex. 8 | Absorbing Agent ((7) | PEG600 | 2% | 92.75 | −0.53 | 3.29 | 6.12 | 92.02 | 81.83 | — | — | — | — | — |
| Ex. 9 | Absorbing Agent (8) | PEG2,000 | 2% | 93.74 | −0.50 | 2.65 | 4.87 | 93.19 | 84.50 | — | — | — | — | — |
| Ex. 10 | Absorbing Agent (9) | PEG6,000 | 2% | 93.96 | −0.35 | 2.46 | 4.62 | 93.46 | 85.14 | — | — | — | — | — |
| Ex. 11 | Absorbing Agent (10) | PEG6,000 | 0.1% | 90.21 | −0.71 | 5.01 | 9.57 | 88.98 | 75.07 | — | — | — | — | — |
| Ex. 12 | Absorbing Agent(11) | PEG6,000 | 0.5% | 91.47 | −0.51 | 3.91 | 7.43 | 90.60 | 78.71 | 38.2 | 6.2 | 326 | 30.3 | 9.3 |
| Ex. 13 | Absorbing Agent(12) | PEG6,000 | 4% | 95.16 | −0.39 | 2.47 | 4.53 | 94.55 | 87.37 | — | — | — | — | — |
| Ex. 14 | Absorbing Agent(13) | Softanol#500 | 0.5% | 91.58 | −0.47 | 4.10 | 7.84 | 90.62 | 78.66 | — | — | — | — | — |
| Ex. 15 | Absorbing Agent(14) | MethoxyPEG2,00 | 0.5% | 91.63 | −0.68 | 3.98 | 7.44 | 90.70 | 78.90 | — | — | — | — | — |
| Com. Ex. 3 | Com. Agent (2) | — | — | 89.97 | −0.55 | 5.92 | 11.53 | 88.34 | 73.49 | 31.0 | 6.0 | 419 | 26.8 | 6.4 |
| Com. Ex. 4 | Com. Absorbing Agent (3) | — | — | 89.26 | −0.48 | 5.65 | 11.14 | 87.85 | 72.62 | 32.6 | 8.9 | 367 | 22.7 | 6.2 |
| Com. Ex. 6 | Com. Absorbing Agent (4) | — | — | 89.53 | −0.74 | 5.65 | 10.90 | 88.07 | 73.06 | — | — | — | — | — |
| Com. Ex. 7 | Com. Absorbing Agent (5) | Diethyleneglycol | 0.5% | 89.43 | −0.87 | 6.39 | 12.28 | 87.62 | 71.96 | — | — | — | — | — |

Abbreviation:
Ex. stands for Example.
Com. Ex. stands for Comparative Example.
Absorbing Agent stands for Particle-Shaped Water Absorbing Agent.
Comparative Absorbing Agent stands for Comparative Particle-Shaped Water Absorbing Agent.
RMC stands for Residual Monomer Content.
Note:
Hunter Lab is of the surface color.

TABLE 4

|  |  | GVs (g/g) | AAP 4.8 Pa (g/g) | Fe Content in Absorbing Agent (ppm by weight) |
|---|---|---|---|---|
| Ex. 16 | Absorbing Agent (15) | 28.6 | 24.4 | 0.70 |
| Ex. 17 | Absorbing Agent (16) | 31.0 | 24.9 | — |
| Ex. 18 | Absorbing Agent (17) | 31.3 | 23.9 | — |
| Com. Ex. 8 | Com. Absorbing Agent (6) | 28.3 | 23.7 | 0.64 |
| Com. Ex. 9 | Com. Absorbing Agent (7) | 29.4 | 20.8 | 9.21 |

Abbreviation:
Ex. stands for Example.
Com. Ex. stands for Comparative Example.
Absorbing Agent stands for Particle-Shaped Water Absorbing Agent.
Comparative Absorbing Agent stands for Comparative Particle-Shaped Water Absorbing Agent.

<Explanation on Tables 2 to 4>

The particle-shaped water absorbing agents (5) to (14) prepared by polymerization performed by adding a compound having a polyoxyethylene group to an unsaturated-monomer aqueous solution in Examples 6 to 15 showed higher L values than the comparative particle-shaped water absorbing agents (2) to (5). The L value indicates the surface color (whiteness) of the particles. This explains that these particle-shaped water absorbing agents (5) to (14) were improved in whiteness.

Further, the particle-shaped water absorbing agents (5), (6), and (11) were slightly higher in GEX than the comparative particle-shaped water absorbing agents (2) and (3). This explained that the particle-shaped water absorbing agents (5), (6), and (11) were more excellent than the comparative particle-shaped water absorbing agents (2) and (3) in physical properties. Further, the particle-shaped water absorbing agents (15), (16), and (17) prepared by surface cross-linking of the particle-shaped water absorbing agents (5), (6), and (11) respectively were excellent in Absorption Against Pressure (AAP4.8 kPa) than the comparative particle-shaped water absorbing agents (6), and (7).

Moreover, too light Fe content did not allow the polymerization as in Comparative Example 5, or gave low physical property as in Comparative Example 9.

The comparative particle-shaped water absorbing agent (5) prepared from the compound whose oxyethylene group was small in molecular weight showed poor whiteness.

Example 19

Into a propylene container of 80 mm in internal diameter and 1 L in volume, which was wrapped with expanded polystyrene acting as a thermal insulator, a solution (A) was prepared, which contained 184.01 g of acrylic acid, 1.29 g of polyethyleneglycoldiacrylate (molecular weight 523), 1.125 g of 1.0 wt % diethylenetriamine 5 acetate 3 sodium aqueous solution, and 4.50 g of 10 wt % 2,2'-thiodiethanol aqueous solution. Then, the solution (A) was mixed with a solution (B), which contained 153.74 g of 48.5 wt % sodium hydroxide aqueous solution and 145.15 g of ion exchanged water adjusted to 50° C. The mixing of the solutions (A) and (B) was carried out in such a manner that the solution (B) was quickly added in the solution (A) stirred with a magnetic stirrer. In this way, a monomer aqueous solution (C) was prepared. Due to neutralization heat and dissolving heat, temperature of the monomer aqueous solution (C) was increased to about 100° C. In the monomer aqueous solution (C), p-methoxyphenol content was approximately 70 ppm by weight, and protoanemonin content, furfural content, β-hydroxypropione acid content, acrylic acid dimmer content were ND (less than 1 ppm by weight). Moreover, phenothazien content was 0 ppm by weight, aldehyde content and maleic acid content were 1 ppm by weight or less, and acetic acid content and propionic acid content were 200 ppm by weight.

Next, into the monomer aqueous solution (C), 10.2 g of 3 wt % sodium persulfate aqueous solution was added with stirring. Immediately after that, the monomer aqueous solution was poured in a stainless vat sized 250×250 mm at bottom and internally coated with Teflon (registered trademark) without a lid thereon, the container being heated to 100° C. by using a hot plate (NEO HOT PLATE H1-1000 (Inouchi Seieido Co., Ltd.). The stainless vat had a size of 250×250 mm at bottom, 640×640 mm on top surface, and 50 mm in height, and a trapezoidal cross-sectional shape and is opened on the top.

Soon after the monomer aqueous solution (C) was poured in the vat, the polymerization was started. The polymerization was carried on with vapor and swelling foaming in all direction and then shrinking to a size slightly larger than the bottom surface. The swelling and shrinking took place in about 1 min. After kept in the polymer vessel for 4 min, the hydrous polymer (hydrous gel) was taken out therefrom. These procedures were carried out atmospheric environment.

The resultant hydrous polymer (hydrous gel) was crushed by a meat chopper, thereby obtaining a hydrous polymer (fragmented gel particles) of several mm in size.

The fragmented gel particles was spread over a 20-mesh (mesh size: 850 µm) metal net and dried at 180° C. for 30 min with hot air. The dried was crushed with a roll mill (WML-type roll crusher, made by Inoguchi Giken Co., Ltd.), and then classified with JIS standard sieves of 850 µm and 150 µm mesh sizes. In this way, a particle-shaped water absorbing agent (18) (solid content 96 wt %) was obtained.

Properties of the resultant particle-sized water absorbing agent (18) are shown on Table 5.

Comparative Example 10

Into a propylene container of 80 mm in internal diameter and 1 L in volume, which was wrapped with expanded polystyrene acting as a thermal insulator, a solution (A) was prepared, which contained 184.01 g of acrylic acid (1) and 1.29 g of polyethyleneglycoldiacrylate (molecular weight 523). Then, the solution (A) was mixed with a solution (B), which contained 153.74 g of 48.5 wt % sodium hydroxide aqueous solution (Fe 0.5 ppm by weight (as $Fe_2O_3$) and copper N.D. (as CuO)), and 145.15 g of ion exchanged water adjusted to 50° C. The mixing of the solutions (A) and (B) was carried out in such a manner that the solution (B) was quickly added in the solution (A) stirred with a magnetic stirrer. In this way, a monomer aqueous solution (C) was prepared. Due to neutralization heat and dissolving heat, temperature of the monomer aqueous solution (C) was increased to about 100° C.

Next, into the monomer aqueous solution (C), 10.2 g of 3 wt % sodium persulfate aqueous solution was added with stirring. Immediately after that, the monomer aqueous solution was poured in a stainless vat sized 250×250 mm at bottom and internally coated with Teflon (registered trademark) without a lid thereon, the container being heated to 100° C. by using a hot plate (NEO HOT PLATE H1-1000 (Inouchi Seieido Co., Ltd.). The stainless vat had a size of 250×250 mm at bottom, 640×640 mm on top surface, and 50 mm in height, and a trapezoidal cross-sectional shape and is opened on the top.

Soon after the monomer aqueous solution (C) was poured in the vat, the polymerization was started. The polymerization was carried on with vapor and swelling foaming in all direction and then shrinking to a size slightly larger than the bottom surface. The swelling and shrinking took place in about 1 min. After kept in the polymer vessel for 4 min, the hydrous polymer (hydrous gel) was taken out therefrom. These procedures were carried out atmospheric environment.

The resultant hydrous polymer (hydrous gel) was crushed by a meat chopper, thereby obtaining a hydrous polymer (fragmented gel particles) of several mm in size.

The fragmented gel particles was spread over a 20-mesh (mesh size: 850 μm) metal net and dried at 180° C. for 30 min with hot air. The dried was crushed with a roll mill (WML-type roll crusher made by Inoguchi Giken Co., Ltd.), and then classified with JIS standard sieves of 850 μm and 150 μm mesh sizes. In this way, a comparative particle-shaped water absorbing agent (8) (solid content 96 wt %) was obtained.

Properties of the resultant comparative particle-shaped water absorbing agent (8) are shown on Table 5.

TABLE 5

| | | GVs (g/g) | Soluble Content (%) | RMC (ppm by weight) | Hunter Lab | | | | Hunter Lab L (after exposure) |
| | | | | | L (before exposure) | b | GEX | CPI | |
|---|---|---|---|---|---|---|---|---|---|
| Ex. 19 | Absorbing Agent (1) | 33 | 7.7 | 280 | 92.5 | 0.03 | 24.5 | 8.7 | 78.5 |
| Com. Ex. 10 | Com. Absorbing Agent (8) | 33 | 8.8 | 320 | 90.9 | 4.3 | 23.0 | 7.2 | 68.5 |

Abbreviation:
Ex. stands for Example.
Com. Ex. stands for Comparative Example.
Absorbing Agent stands for Particle-Shaped Water Absorbing Agent.
Comparative Absorbing Agent stands for Comparative Particle-Shaped Water Absorbing Agent.
RMC stands for Residual Monomer Content.
Note:
Hunter Lab is of the surface color.
* 70 +/− 1° C., relative humidity 65 +/− 1% for 7 days.

SUMMARY

As shown in Table 5, the particle-shaped water absorbing agent and the production method thereof according to the present invention is high in the color (L) before the coloring experiment (before exposure), but also the color (K) after the experiment (after exposure). Thus, the particle-shaped water absorbing agent and the production method thereof according to the present invention give whiteness that is sufficient in practical usage. Further, the particle-shaped water absorbing agent and the production method thereof according to the present invention are improved in terms of water solubility and residual monomers.

Example 20

A absorbent core was prepared in the same manner as in Example 5, except that the particle-shaped water absorbing agent (15) obtained in Example 16 was used instead. The absorbent core was evaluated. The evaluation showed that rewetting amount was 3.2 g, and outer appearance thereof was white and gave sensation of cleanness visually.

Industrial Applicability

When a particle-shaped water absorbing agent according to the present invention is used in a thin absorbing core for diaper or the like, better whiteness in particle surface color in the particle-shaped water absorbing agent gives sensation of cleanness, compared with conventional absorbing cores. Further, the use of the particle-shaped water absorbing agent according to the present invention provides excellent absorbency (excellent AAP property), which the conventional arts cannot obtain.

The invention claimed is:

1. A particle-shaped water absorbing agent containing a resin of an acrylic acid and/or a salt thereof in a range of 70 to 99.9% by weight to the particle-shaped water absorbing agent, the particle-shaped water absorbing agent having a surface color of a Hunter b value in a range of −5 to 10 and a Hunter L value in a range of 90 to 100, and having a cross-linking absorption property index (CPI) in a range of 1 to 100, the CPI defined by the following equations:

$$GEX=(GVs+17)/Ln \text{ ( amount of extracted water-soluble polymer)}; \quad \text{Equation 1:}$$

$$CPI=(GEX/\text{residual monomer content})\times 100 \text{ if the residual monomer content is not less than 20 ppm by weight; and} \quad \text{Equation 3:}$$

$$CPI=GEX-\text{residual monomer amount if residual monomer content is less than 20 ppm by weight}, \quad \text{Equation 4:}$$

where GVs is gel volume in saline, Ln (amount of extracted water-soluble polymer) is a logarithm natural of amount of extracted water-soluble polymer; and wherein the particle-shaped water absorbing agent further contains one or more of components (i) to (iii):

(i) an N-oxyl compound in a range of 0.01 to 10 ppm by weight; and a methoxyphenol compound in a range of 0 to 20 ppm by weight;

(ii) a methoxyphenol compound in a range of 0.01 to 20 ppm by weight; and a manganese compound in a range of 0.01 to 10 ppm by weight (as $MnO_2$);

(iii) a polyalkyleneglycol of weight average molecular weight of 300 to 50000; and iron in a range of iron content in a range of 0.001 to 5 ppm by weight.

2. The particle-shaped water absorbing agent as set forth in claim 1 containing crosslinking agents comprising 1,4-butanediol and propylene glycol.

3. The particle-shaped water absorbing agent as set forth in claim 1, further containing a chelating agent.

4. The particle-shaped water absorbing agent as set forth in claim 3, wherein the chelating agent is a non-polymer amino polyvalent carboxylic acid compound or a non-polymer amino polyvalent phosphoric acid compound having a weight average molecular weight of 5000 or below.

5. The particle-shaped water absorbing agent as set forth in claim 4, wherein the chelating agent has a weight average molecular weight of from 100 to 1000.

6. The particle-shaped water absorbing agent as set forth in claim 1, wherein the CPI is in a range of 1 to 50.

7. The particle-shaped water absorbing agent as set forth in claim 1, wherein the Hunter b value is in a range of −5 to 5.

8. The particle-shaped water absorbing agent as set forth in claim 1, satisfying at least one of the followings:
- (a) the particle-shaped water absorbing agent contains particles smaller than 150 μm in particle size by 0 to 5% by weight, and has a mass medium particle size (D50) in a range of 200 to 600 μm and a logarithmic standard deviation (σξ) of particle size distribution in a range of 0.20 to 0.40;
- (b) the particle-shaped water absorbing agent has an AAP of 20 g/g or more for 0.90wt% saline under pressure of 1.9kPa or 4.8kPa for 60 min; and
- (c) the particle-shaped water absorbing agent has SFC of 5 ($cm^3 \cdot s \cdot 10^{-7}/g$) or more for 0.69wt % saline.

9. The particle-shaped water absorbing agent as set forth in claim 1, wherein the polyalkyleneglycol is non-radically polymerizable.

\* \* \* \* \*